US010275969B2

(12) United States Patent
Hussain et al.

(10) Patent No.: US 10,275,969 B2
(45) Date of Patent: Apr. 30, 2019

(54) METHOD AND SYSTEM FOR ITEM AUTHENTICATION AND CUSTOMIZATION

(71) Applicant: United States Postal Service, Washington, DC (US)

(72) Inventors: Khalid Hussain, Kansas City, MO (US); Marie Therese Dominguez, Arlington, VA (US); David E. Failor, Rockville, MD (US); William G. Ackerman, Washington, DC (US)

(73) Assignee: United States Postal Service, Washington, DC (US)

( * ) Notice: Subject to any disclaimer, the term of this patent is extended or adjusted under 35 U.S.C. 154(b) by 0 days.

(21) Appl. No.: 14/995,050

(22) Filed: Jan. 13, 2016

(65) Prior Publication Data
US 2016/0133078 A1 May 12, 2016

Related U.S. Application Data

(63) Continuation-in-part of application No. 13/790,559, filed on Mar. 8, 2013, now Pat. No. 9,291,559.
(Continued)

(51) Int. Cl.
G06K 7/10 (2006.01)
G07D 7/005 (2016.01)
(Continued)

(52) U.S. Cl.
CPC .......... *G07D 7/0053* (2013.01); *B41J 3/4075* (2013.01); *B42D 25/29* (2014.10);
(Continued)

(58) Field of Classification Search
CPC ...... G01N 21/64; G01N 21/643; G07D 7/122; B41K 3/00
See application file for complete search history.

(56) References Cited

U.S. PATENT DOCUMENTS 4,082,873 A * 4/1978 Williams .............. G09F 3/0292
428/42.1
4,121,003 A 10/1978 Williams
(Continued)

FOREIGN PATENT DOCUMENTS

CN 101727605 A 6/2010
CN 102163291 A 8/2011
(Continued)

OTHER PUBLICATIONS

International Search Report and Written Opinion from PCT/US13/29904; dated May 13, 2013.
(Continued)

*Primary Examiner* — David P Porta
*Assistant Examiner* — Shun Lee
(74) *Attorney, Agent, or Firm* — Knobbe Martens Olson & Bear LLP

(57) ABSTRACT

A method of illuminating an item is disclosed. The method includes applying adhesive to the item, interspersing a taggant in the adhesive, illuminating the item with an excitation signal, sensing luminescence emitted by the taggant in response to illumination by the excitation signal, and determining the authenticity of the item based on the sensed emitted luminescence. The item can include any item benefited by authentication, and can include a postage stamp. A method of customizing an item is disclosed. This can include the steps of preparing a substrate, applying a security feature to the substrate, printing non-customized information on the substrate, receiving image information, and printing the image information on the substrate.

19 Claims, 15 Drawing Sheets

Related U.S. Application Data

(60) Provisional application No. 61/609,163, filed on Mar. 9, 2012.

(51) Int. Cl.

| | | |
|---|---|---|
| *G07D 7/121* | (2016.01) | |
| *G07D 7/20* | (2016.01) | |
| *B41J 3/407* | (2006.01) | |
| *G06K 19/06* | (2006.01) | |
| *G01N 21/64* | (2006.01) | |
| *G06K 19/14* | (2006.01) | |
| *B42D 25/29* | (2014.01) | |
| *B42D 25/382* | (2014.01) | |
| *B42D 25/387* | (2014.01) | |
| *B42D 25/45* | (2014.01) | |
| *G09F 3/00* | (2006.01) | |
| *G09F 3/10* | (2006.01) | |
| *G07D 7/1205* | (2016.01) | |

(52) U.S. Cl.
CPC ......... *B42D 25/382* (2014.10); *B42D 25/387* (2014.10); *B42D 25/45* (2014.10); *G01N 21/643* (2013.01); *G06K 19/06028* (2013.01); *G06K 19/14* (2013.01); *G07D 7/121* (2013.01); *G07D 7/1205* (2017.05); *G07D 7/20* (2013.01); *G09F 3/0294* (2013.01); *G09F 3/0297* (2013.01); *G09F 3/10* (2013.01); *G01N 2021/6421* (2013.01)

(56) References Cited

U.S. PATENT DOCUMENTS

| | | | | |
|---|---|---|---|---|
| 4,490,410 | A | * | 12/1984 | Takiyama ............ B05D 1/286 427/146 |
| 5,042,842 | A | | 8/1991 | Green et al. |
| 5,446,705 | A | * | 8/1995 | Haas ..................... B32B 27/08 116/200 |
| 5,605,738 | A | * | 2/1997 | McGinness ........... B41M 3/144 250/365 |
| 5,683,774 | A | * | 11/1997 | Faykish ............... G03H 1/0011 283/101 |
| 6,592,972 | B1 | | 7/2003 | Trantoul |
| 7,185,453 | B2 | | 3/2007 | Spear et al. |
| 2002/0130303 | A1 | | 9/2002 | Muth et al. |
| 2002/0131618 | A1 | | 9/2002 | Ahlers et al. |
| 2003/0140017 | A1 | | 7/2003 | Patton et al. |
| 2003/0148055 | A1 | | 8/2003 | Scheubner |
| 2004/0023008 | A1 | | 2/2004 | Rosset |
| 2004/0070194 | A1 | | 4/2004 | Janetzke et al. |
| 2006/0127649 | A1 | | 6/2006 | Keller et al. |
| 2006/0224403 | A1 | | 10/2006 | Whitehouse |
| 2007/0108757 | A1 | | 5/2007 | Buck |
| 2007/0119951 | A1 | | 5/2007 | Auslander et al. |
| 2008/0283612 | A1 | | 11/2008 | Fearn |
| 2009/0122349 | A1 | | 5/2009 | Bala et al. |
| 2011/0193337 | A1 | | 8/2011 | Tziovaras et al. |
| 2014/0230207 | A1 | | 8/2014 | Oraw et al. |

FOREIGN PATENT DOCUMENTS

| | | |
|---|---|---|
| DE | 35 14 852 A1 | 10/1986 |
| JP | H06 297883 A | 10/1994 |
| WO | WO 94/11203 A1 | 5/1994 |
| WO | WO 2004/102490 A1 | 11/2004 |
| WO | WO 2013/134654 A1 | 9/2013 |

OTHER PUBLICATIONS

'Create Your Own Stamps!', Jul. 30, 2005, Retrieved on Apr. 30, 2013 from the Internet, URL: http//web.archive.org/web/20050730235418lhttp://www.zazzle.com/stamps/.

Swinehart, the Beer-Lambert Law, Journal of Chemical Eduction, vol. 39, No. 7, pp. 333-335 (Year: 1962).

\* cited by examiner

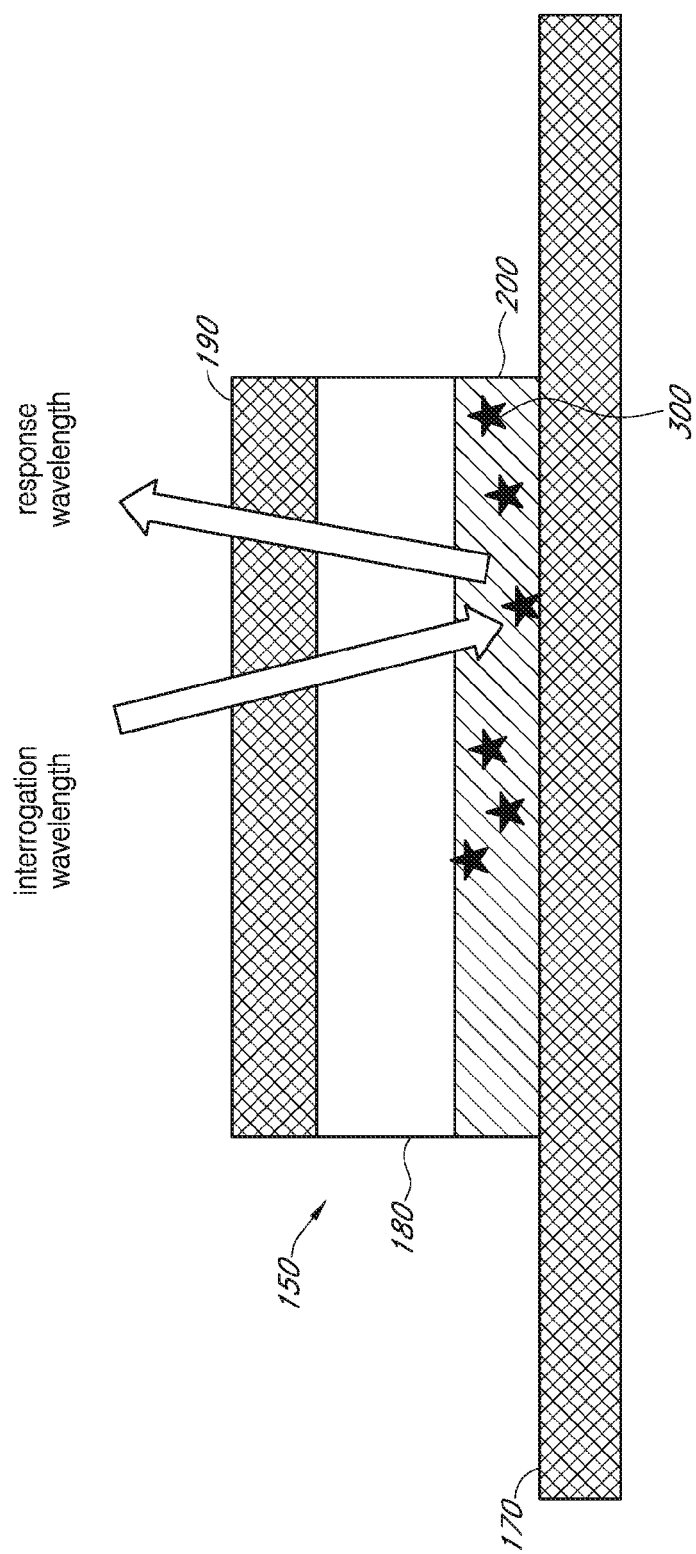

METHOD AND SYSTEM FOR ITEM AUTHENTICATION AND CUSTOMIZATION

CROSS-REFERENCE TO RELATED APPLICATIONS

This application is a continuation-in-part of U.S. application Ser. No. 13/790,559, filed Mar. 8, 2013, which in turn claims priority to U.S. Provisional Application 61/609,163, filed Mar. 9, 2012, the entire contents of which are herein incorporated by reference. Any and all priority claims identified in the Application Data Sheet, or any correction thereto, are hereby incorporated by reference under 37 CFR 1.57.

BACKGROUND

Field of the Development

This application relates generally to custom systems and methods for authenticating articles.

Description of the Related Technology

Counterfeiting articles of many kinds is a serious problem worldwide, causing great loss of revenues to legitimate businesses and to individuals. Counterfeiters have produced articles that are very difficult to distinguish from the genuine articles, taking sales revenues from the producers of genuine articles and impacting legitimate business' reputations when the counterfeit articles have inferior quality and/or non-existent manufacturers' support. Similarly, problems and losses occur due to counterfeiting of articles used for financial transactions or identification, such as postage stamps, banknotes, credit cards, drivers' licenses, passports, and immigration documents. Even when genuine articles have been marked with authentication markings such as watermarks, special papers, and holograms which are difficult to replicate, counterfeiters have managed to produce articles that appear genuine. The general availability of newer replication technology such as high-resolution image scanners, laser copiers and printers, and color-accurate color copiers and printers has enabled counterfeiters to produce more credible counterfeit articles.

Postage stamps have historically been produced by governing entities. Their intended purpose is to show that a certain fee has been paid to post a mail piece for delivery. Very shortly after the innovation of the postage stamp, some people began to counterfeit stamps and some people began to save and collect stamps.

These technological developments of replication hardware continue to progress rapidly, as does the development of computer hardware and software that support them. Thus it is useful to have additional ways to mark articles for authentication with greater security. Greater security may be achieved by making authentication markings more difficult for counterfeiters to detect and interpret, by incorporating greater complexity into the markings, and by making replication by counterfeiters more difficult. Combining multiple kinds of marking indicia can further increase the complexity of detection, interpretation, and replication, thus providing even better security. Considering the security issue from another point of view, it is not desirable to use the same means that generated the visible appearance of an article to authenticate it, as the visible appearance is becoming easier to replicate.

Many methods have been known to authenticate valuable articles. Some known methods include imprinting a white-light hologram on an item for authentication or imprinting reflective and diffractive indicia which display distinctive images that are difficult to counterfeit on an item for authentication. Other known methods include incorporation of distinctive fibers into the articles, such fibers being detectable by visual observation, microwave irradiation, or other means.

Thus, a covert optical feature with ability to be detected via electronic authentication apparatus and that cannot be reproduced by common visible graphic copying and printing means can provide improved security is described herein.

Stamp collecting has likewise affected postal business. Specifically, stamp collecting encouraged stamp issuing entities to produce stamps which not only function as a proof of payment device, but which are also topically and/or aesthetically appealing. Traditionally subjects of broad appeal such as landmarks, indigenous plants and animals, and nationally known public figures have been featured on postage stamps. In the 21st century, with the advent of new technology, the capability exists to economically produce small quantities of postage stamps which appeal to a narrower audience. This has sparked the emergence of "personalized postage stamps."

Personalized postage is currently available in the United States and other countries. Private companies have contract agreements with the USPS to create postage stamps using customer submitted images and text. However, these stamps require a large portion of the face of the stamp be utilized for scrambled indicia to ensure compatibility with USPS automation equipment. These large indicia reduce the available image size, and detract from the overall aesthetic appeal. Some postal agencies in other countries produce personalized postage stamps, but their design utilizes a perforation between the actual valid postage and the personalized segment of the stamp. If the two parts are separated on the perforation, the personalized design is simply a sticker with no postage value.

SUMMARY

Some embodiments relate to a method of authenticating an item. In some embodiments, the method of authenticating an item can include, for example, applying an adhesive to the item, interspersing a taggant in the adhesive, which taggant can emit luminescence in response to an excitation signal, illuminating the item with the excitation signal, sensing the emitted luminescence from the taggant, and determining the authenticity of the item based on the sensed emitted luminescence.

In some aspects of the method of authenticating an item, the excitation signal can be electromagnetic energy which can be energy within a predetermined spectrum. In some aspects, the electromagnetic energy can be IR and/or UV.

In some aspects of the method of authenticating an item, the emitted luminescence can be electromagnetic energy which can be energy within a predetermined spectrum. In some aspects, the emitted luminescence can be IR and/or UV. In some aspects of the method of authenticating the item, both the excitation signal and the emitted luminescence are IR.

Some embodiments relate to a method of authenticating an item through a substrate. In some embodiments, the method of authenticating an item through a substrate can include, for example, applying a taggant to the item, which taggant can, for example, emit luminescence in response to illumination by an excitation signal, illuminating a substrate with an excitation signal. In some embodiments, the properties of the excitation signal allow the excitation signal to pass through the substrate to excite luminescence by the taggant. In some embodiments, the method of authenticating an item through a substrate can include sensing emitted luminescence and determining the authenticity of the item based on the sensed luminescence. In some embodiments, the properties of the emitted luminescence allow the emitted luminescence to pass through the substrate to be sensed.

In some aspects of the method of authenticating an item through a substrate, the relative transparency of the substrate is determined across a portion of the electromagnetic spectrum. In some aspects of the method of authenticating an item through a substrate, the taggant is excited by the excitation signal having a wavelength corresponding to high relative transparency of the substrate, and/or the taggant emits luminescence having a wavelength corresponding to a high relative transparency of the substrate in response to illumination by the excitation signal.

In some aspects of the method of authenticating an item through a substrate, the excitation signal can be electromagnetic energy which can be energy within a predetermined spectrum. In some aspects of the method of authenticating an item through a substrate, the excitation signal can be IR and/or UV.

In some aspects of the method of authenticating an item through a substrate, the emitted luminescence can be electromagnetic energy which can be energy within a predetermined spectrum. In some aspects of the method of authenticating an item through a substrate, the emitted luminescence can be IR and/or UV. In some aspects of the method of authenticating an item through a substrate, both the excitation signal and the emitted luminescence can be IR.

Some embodiments relate to a method of creating customized postage stamps. In some embodiments, the postage stamps can include a substrate, adhesive and a printing, and the method can include preparing the substrate, applying a security feature to the postage stamps, printing non-customized information onto the substrate, which non-customized information can include an indication of stamp value and a stamp characteristic, receiving image information, and printing the image information onto the substrate.

In some aspects of the method of creating customized postage stamps, preparing the substrate includes receiving a sheet of stamp paper, applying an adhesive to the substrate, and/or dividing the substrate into postage stamp sized pieces. In some aspects of the method of creating customized postage stamps, the substrate is divided into postage stamp sized pieces via perforations.

In some aspects of the method of creating customized postage stamps, applying the security feature comprises printing a security feature onto the substrate, integrating a feature into the substrate, and/or adding a taggant to the substrate.

In some aspects, the method of creating customized postage stamps can further include determining if the received image information meets image information requirements, and/or resizing the image information to fit on a customized postage stamp. In some aspects of the method of creating customized postage stamps the printing of the non-customized information and the printing of the image information are simultaneous or the printing of the non-customized information and the printing of the image information are temporally spaced.

Some embodiments relate to a system for authenticating an item. In some embodiments the system can include, for example, a label or identifier that can include a substrate, adhesive applied to a portion of the substrate, and a taggant interspersed in the adhesive. In some embodiments, the system can include a detector that can include an illuminator that emits a signal that excites the taggant to luminesce, and a sensor that detects luminescence emitted by the taggant.

In some aspects of the system, the item can further include a printing. In some aspects of the system, the substrate is substantially planar and comprises a first side parallel to a second side. In some aspects of the system, the adhesive is, for example, applied to the first side of the substrate, and/or the printing is, for example, applied to the second side of the substrate. In some aspects of the system, the adhesive affixes the item to an object.

In some aspects of the system, the signal emitted by the illuminator passes through the substrate before it excites the taggant to luminesce, and/or the luminescence emitted by the taggant passes through the substrate before it is detected by the sensor.

Some embodiments relate to a method of authenticating an item. In some embodiments, the method can include, for example, illuminating the item with the excitation signal. In some embodiments, the item can include an adhesive with an interspersed taggant that emits luminescence in response to an excitation signal. In some embodiments, the method further includes, sensing the emitted luminescence from the taggant and determining the authenticity of the item based on the sensed emitted luminescence.

Some embodiments relate to a method of authenticating an item through a substrate. In some embodiments, the method includes illuminating a substrate with an excitation signal. The substrate can include, for example, a taggant that emits luminescence in response to illumination by an excitation signal. In some embodiments of the method, the excitation signal passes through the substrate to excite luminescence by the taggant. In some embodiments, the method further includes, sensing emitted luminescence, which luminescence can pass through the substrate to be sensed. In some embodiments, the method further includes determining the authenticity of the item based on the sensed luminescence.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

DESCRIPTION OF THE DRAWINGS

FIG. 1A illustrates a cross-sectional view of one embodiment of a basic mechanism of an item validation system, showing the pathway of an excitation light as it travels through the print and the substrate to the luminescent additive eliciting the luminescent response that radiates back through the substrate.

Figure 1B:
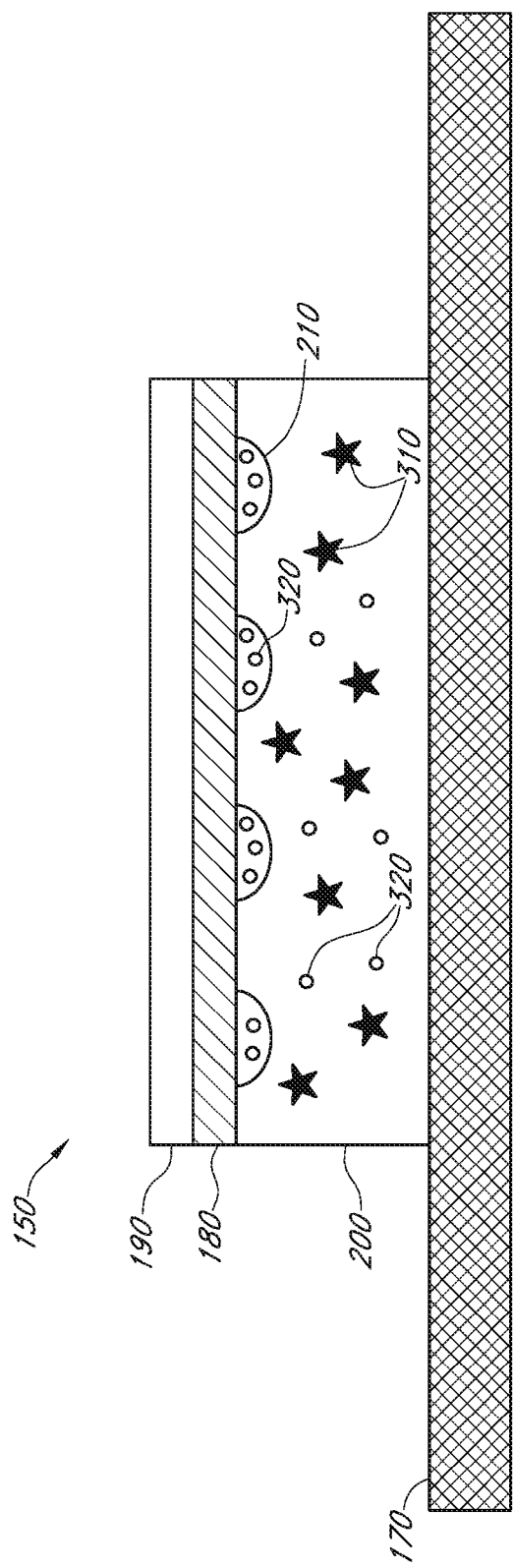
FIG. 1B illustrates a cross-sectional view of one embodiment of an item validation system having more than one type of taggant.

Various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

The features, aspects and advantages of the present development will now be described with reference to the drawings of several embodiments which are intended to be within the scope of the embodiments herein disclosed. These and other embodiments will become readily apparent to those skilled in the art from the following detailed description of the embodiments having reference to the attached figures, the development not being limited to any particular embodiment(s) herein disclosed.

The system described herein provides an improved authentication system that stimulates, detects and recognizes a response from an indicator in an item to be validated or authenticated. In some embodiments, the system described herein provides an improved authentication system that stimulates, detects, and recognizes infrared ("IR") response from an indicator in an item to be validated or authenticated. In some embodiments, the system described herein provides an improved authentication system that stimulates, detects, and recognizes IR response from a luminescent adhesive incorporated into the item that is to be validated or authenticated. This IR response can be, in some embodiments, stimulated, detected, and recognized through the substrate of an item to be validated or authenticated.

In one embodiment, the system combines the use of compounds that produce luminescence when being subjected to illumination in a designated spectrum with detectors that are capable of detecting the luminescent response and then analyze the response's optical signature. In some embodiments, the compounds can luminesce in a designated portion of the electromagnetic spectrum in response to illumination with infrared, visible, or ultraviolet. In some embodiments, the luminescence of the compounds can be in the same spectral regions as the illumination, and in some embodiments, the luminescence of the compounds can be in different spectral regions than the illumination. In one specific embodiment, the compounds are illuminated with IR and likewise luminesce in IR.

The system can comprise two components: 1) a unique optical taggant material embedded into one or several components of the item to be authenticated, and 2) a corresponding detector to authenticate the presence of the embedded taggant.

Generally, a system and label are described herein whereby a taggant is introduced into an adhesive or backing of a label. The label may be a postal stamp, tax stamp, product label or other substrate with adhesive which is used to impart a level of security or impart some information. In one embodiment, the item to be authenticated utilizes taggant in the adhesive. In another embodiment, the item to be authenticated utilizes taggant in the paper, ink, or other portion of the item. Advantageously, use of such a system can impart information to identify an item. Further, use of such a system can conceal the security features to inhibit replication of the security features. The detector may emit a signal, wavelength, or spectrum which will interact with the taggant. The detector signal may be referred to as an interrogation wavelength. Upon interaction with the interrogation signal, the taggant may respond by emitting a wavelength, signal, or spectrum, which may be referred to as the response wavelength. These concepts will be explained in more detail below.

FIG. 1 depicts one embodiment of some aspects of an authentication system 100. FIG. 1 depicts a label 150 comprising an adhesive 200, a substrate 180, and printed material 190 on the outward facing surface of the substrate 180. As depicted in FIG. 1, the label 150 is adhered to an object 170 by the adhesive 200. As further depicted in FIG. 1, the label 150 comprises a taggant 300 interspersed in the adhesive 200 of the label 150. The discussion herein is directed toward a label adhered to an object. The label is an exemplary embodiment used for convenience. A person of skill in the art would understand that the article being adhered to an object may be a postage stamp, a sticker, a poster, or any other desired article. A skilled artisan will also understand that to effectuate the authentication system or process the label need not necessarily be adhered to a specific object, or any object. In some exemplary embodiments, the label 150 is a postage stamp, and the object 170 is an envelope or other mail article, but the label 150 and the object 170 are not limited thereto.

In some embodiments, the label 150 can comprise a variety of shapes and sizes and can be made of a variety of materials. In some embodiments, the label 150 can comprise paper, cloth, wood, metal, manmade, or natural materials. In some embodiments, the label 150 can comprise an object of a type that is frequently counterfeited or on which frequent counterfeiting attempts are made. In some embodiments, the label 150 can comprise any object for which authentication is desirable. In some embodiments, the label 150 can comprise an object whose representative value is higher than its inherent value; the label 150 can comprise an object having more value than the sum of its material costs and manufacturing costs. Such objects can include, for example, money, checks, postage, tickets, including airplane tickets, movie tickets, concert tickets, lift tickets, vouchers, or any other similar object. In another embodiment, the label 150 can comprise a protective marking on product packaging, tax stamps, pharmaceutical labels, or apparel and shoe labels. In another embodiment, the label 150 can comprise an identification document such as a passport or immigration document, or any other similar document.

The substrate 180 can comprise a variety of shapes and sizes and can be made of a variety of materials. In some embodiments, the substrate 180 can comprise paper, cloth, wood, metal, manmade, or natural materials. The substrate 180 can comprise any material configured to receive indicia of the label 150. In some embodiments, these indicia of the item can be printed, pressed, embossed, applied, dyed, or otherwise placed on or incorporated into the substrate 180. In one specific embodiment, the substrate 180 can comprise a piece of paper cut or delineated with, for example, perforations for use as a stamp.

The adhesive 200 can comprise a variety of adhesive materials. In some embodiments, the adhesive 200 can comprise a natural or a manmade adhesive. In some embodiments the adhesive 200 can be applied to all or portions of the substrate 180. In one embodiment, and as depicted in FIG. 1, the adhesive 200 covers one side of substrate 180. In one embodiments, the adhesive 200 can comprise the adhesive material on the back of a stamp.

Taggants

In some embodiments, the taggant 300 can comprise a luminescent material, which can be configured to luminesce in response to illumination by an excitation signal. In some embodiments, this excitation signal can be created by a detector device. The excitation signal can illuminate the taggant 300 and excite the luminescent material. The luminescent material, now excited by the excitation signal, luminesces, which luminescence can be detectable by the detector to identify the label 150. In some embodiments, the luminescent material can be configured to luminesce for the duration of its illumination by the excitation signal. In some embodiments, the detector can positively identify the label 150 if the detector detects luminescence or luminescence of a specific wavelength in response to illumination by the excitation signal. The luminescence generated by the taggant 300 in response to the excitation signal can be referred to as an emission pattern or emission signal.

In some embodiments, the taggant 300 may be a phosphorescent taggant. The optical properties may vary for the taggant. For increased security the taggant is preferably phased, meaning the interrogation wavelength is different from the response wavelength. In fluorescent taggants the interrogation wavelength can be higher than the response or fluorescent wavelength. The taggant can be tailored for shift of wavelength between the interrogation wavelength and response wavelength and the response timing or delay of response. Alternatively, the taggant may use a dual phase shift. Meaning the taggant has the ability to have one interrogation wavelength with a shift to X wavelength and another interrogation wavelength with a shift to Y wavelength for response. In this way a broad spectrum interrogation may be used but only one of the shifted wavelengths is scanned for response.

In some embodiments, one or more taggants 300 may be chosen so that the response wavelength matches the interrogation wavelength. In some embodiments, the difference or mismatch between the interrogation and the response wavelength may be used to identify a genuine article or label.

In some embodiments, one or more taggants 300 may be selected based on the intensity or strength of the response wavelength. The strength or intensity of the response wavelength maybe used to authenticate or verify genuine articles or labels. For example, a taggant 300 which emits a high or strong response wavelength may be chosen to provide a first response wavelength in combination with a taggant 300 which emits a weaker second response wavelength, which masks the detection band wavelength.

In some embodiments, the luminescent material may be configured to continue to luminesce for some duration of time after it has been illuminated by the excitation signal. The duration of time that the luminescent material luminesces, and the change of intensity of the luminescence over time can be characterized by luminescent decay. In some embodiments, the taggant 300 can comprise a luminescent material having known luminescent decay. In such embodiments, the luminescent decay of the luminescent material can be detected by the detector in response to an excitation signal of known intensity and duration and can be used to identify the label 150.

The taggants 300 can comprise a variety of features, sizes, and materials. In one embodiment, the taggants 300 can comprise particles. These particles may have a dimension of approximately, 0.0001 mm, 0.0005 mm, 0.001 mm, 0.005 mm, 0.01 mm, 0.05 mm, 0.1 mm, 0.5 mm, 1 mm, 10 mm, 25 mm, or any other desired size. In some embodiments the taggants 300 can comprise a variety materials, including, for example, natural or manmade materials. In some embodiments, the taggants 300 can comprise ceramics, and can specifically comprise inorganic optical ceramics. In some embodiments, the taggants 300 can be configured to be environmentally stable, which can include, for example, thermal stability, chemical stability, or stability with regards to any other desired environmental factors such as, for example, humidity or pressure. In some embodiments, more than one type of taggant 300 may be used at a time. For example, the label 150 may comprise both an optical ceramic and an IR illuminated taggant, or one taggant 300 with a response wavelength in the visible spectrum and a second taggant 300 having a response wavelength in the IR spectrum. These combinations are exemplary only, and are not intended to limit the scope of this application.

In some embodiments, the taggant 300 may be an optical taggant. A preferred taggant 300 is one that is stable in the adhesive. In some embodiments, a taggant 300 that deteriorates over a known time may be advantageous. In some embodiments, the taggant 300 may produce a response wavelength having an upshift or a downshift from the interrogation wavelength, and may have an interrogation wavelength or response wavelength in the UV, visible or IR spectrums. In a high volume application such as with conveyor belts the interrogation wavelength is preferably in the IR or UV spectrum, whereas high intensity visible light may damage the rubber or other organic components of a conveyor system.

Taggant 300 may be a variety of materials, such as organic dyes, pigments, metallic oxides, inorganic ceramics, or the like. In some embodiments, the taggant 300 may be quantum dots or the like which may be tuned to varying frequencies. In one embodiment, the taggant 300 is a metallic oxide which tends to be stable for long periods and is easily handled. Rare earth oxides like lanthanum oxide and the like may have desirable characteristics. Other metal oxides which are tunable to various frequencies may be employed and may be advantageously used due to the tunability and ability to add choices to the strata and inks.

Advantageously, the use of environmentally stable taggants 300 can allow the use of the taggants in difficult environments, and can increase manufacturing flexibility relating to the time of application of the taggants 300 in the manufacturing process, the location of the taggants 300 in a manufactured item, and finishing process performed after the application of the taggants 300. Specifically, and in contrast to dyes or other identification techniques currently used, the use of environmentally stable taggants 300 expands applicability of taggants 300. Further, due to the physical features and attributes of the taggants 300, the taggants 300 are very difficult to isolate, and are thus very difficult to reverse engineer. This provides an additional layer of security as it further complicates the process of creating counterfeit taggants 300.

In one specific embodiment, taggants 300 comprising inorganic optical ceramics can be configured to operate in a specific region of the light spectrum, such as, for example, the IR region, the visible light region, or the UV region. In some embodiments, the taggants 300 operate in non-visible portions of the light spectrum. A human eye may be used a as a detector in some applications where the response wavelength of the taggant 300 is in the visible spectrum. For example, the taggant 300 may glow in a desired color in the visible spectrum when interrogated with IR, visible or UV light, thus showing a user the label or strata within the label 150 are genuine. A detector would be needed in the case of response wavelengths outside the visible spectrum.

In some embodiments, the taggants 300 can be uniquely identifiable, to determine information such as manufacturing batch, approximate time of manufacture, or other information. In addition to the covert luminescence level of security, they carry a forensic (laboratory) level. In other embodiments, other taggants or fluorescents are used.

In some embodiments, the taggants 300 can comprise materials, sizes, and luminescent materials that are safe for use in a variety of applications. In some embodiments, the taggants 300 can be safe for use in food packaging and toys. In some embodiments, the taggants 300 can be configured for passing health and safety tests such as, for example, the EN71-3 and TPCH tests.

In some embodiments, the taggants 300 can be configured to be visible or invisible to the human eye. In some embodiments, the taggants 300 can comprise dimensions and materials that prevent detection by the human eye. In some embodiments, the taggants 300 can be located on or in the adhesive 200 to prevent detection by the human eye. Thus, in one embodiment, and as depicted in FIG. 1A, the taggants 300 can comprise an integral portion of the label 150, and can thereby be invisible to the human eye. Advantageously, taggants 300 having properties or placements which prevent detection by the human eye can further decrease the likelihood of duplication. Thus, in some embodiments, the taggants 300 can be difficult to duplicate and hard to detect because they are out of the line of sight and are invisible to the naked eye, UV insensitive, and hard to separate from the adhesive 200. The taggant 300 possesses a secure technology in that it is stable thermally and chemically and it has an immeasurable lifetime. In one embodiment, the ceramic is a non-reactive ceramic, withstanding temperatures up to 1000° C. The taggant is lightfast, non-hazardous and is easily integrated into the adhesive coating process.

In some embodiments, the taggant 300 may be used to incorporate informational or other types of security. The shape of an image of the taggant 300 may be screen printed or applied via a number of techniques such as ink-jet printing or the like. The applied taggant 300 can be in many different shapes and sizes, for example, the taggant 300 may be shaped as a logo of a company, an image, a number, name of buyer or seller, or barcodes of various types, applied using a variety of techniques described herein. One label may have several of these at the same time and each may be in a different taggant or the same taggant.

When using an informational image such as a name or the like it may be preferable for the image to be visible to the human eye. Thus the response wavelength of the taggant should be in the visible spectrum although the interrogation wavelength need not be. For information or machine readable images it may be preferable but not necessary to have the response wavelength in the non-visible spectrum like IR. These information images may be scanned by a device which is sensitive to the response wavelength or imaged with a scanner or camera (e.g., IR camera, visible light camera, SLR camera, etc.) for further processing to obtain the image and information. A camera can take a picture of the response and then enhance the image whereby the enhanced image is processed to obtain the barcode and information therefrom.

The label or strata within the label 150 may be mass produced by these processes. In some embodiments, the taggant 300 or a substance containing the taggant 300 may be printed onto the back of a sheet or paper, which is then covered with adhesive to combine the taggant with the adhesive, or may be printed onto a label backing onto which an adhesive label is placed. In some embodiments, the taggant 300 or substance containing the taggant 300 may be printed onto a surface of the object to be covered by the label, and then covered by adhesive. In some embodiments, where the taggant is applied to the label backing, the label is then at a later time the label is removed from the backing and placed on the object. Even though originally printed on the backing, the taggant 300 is combined with the adhesive and carried off with the label and adhesive when the label is applied to the object. In mass production the image or information may remain the same or change with each label or both. These methods may be performed either generally or locally, and may impart an image to the label or the object onto which the label will be placed. For example the logo of the manufacturer may be the same with each label but the barcode or serial number may change for each label. Either of these images may use the same taggant or different taggant.

The label 150, which may be a label or several strata may be chosen depending on the interrogation and response wavelengths. Specifically, the substrate 180 and/or the printed material 190 may be chosen such that the interrogation wavelength can reach the taggant 300 in order to induce a response wavelength. Similarly, the label 150, including the substrate 180 and the printed material 190 may be chosen such that the response wavelength can penetrate the substrate 180 and the printed material 190 and be detected by the detector. The ability of the label 150, including the substrate 180 and the printed material 190, may be referred to as the transmissivity. A high transmissivity of both the response and interrogation wavelengths may be used. In some embodiments, a transmissivity as low as 10% is possible. Choosing the label material may mean that a detector with high sensitivity is needed if the transmissivities are low or a high intensity interrogation signal may be used. These factors may be combined and varied depending on the application. The printing or ink used on a label is also chosen based upon the wavelengths and system requirements.

The substrate 180 can be chosen for its optical properties in regard to the taggant 300 used or taggants used. If a high transmissivity is needed at a certain wavelength then the label 150 or substrate 180 may be matched to that wavelength. Likewise, the taggant 300 may be chosen to allow transmission of interrogation and response wavelengths accordingly. In this way the transmission and reflectance are used to accomplish the goal desired.

FIG. 1B depicts an item validation system having more than one taggant. For example, the adhesive 200 comprises a first taggant 310 and a second taggant 320. In some embodiments, the first taggant 310 and the second taggant 320 are dispersed in the adhesive 200 as desired, to create a response wavelength that shows a particular wavelength, an image, a barcode, or other image as described elsewhere herein. As described elsewhere herein, the first taggant 310 and the second taggant 320 may have differing response wavelengths. In some embodiments, the adhesive 200 comprises a second adhesive area 210. In some embodiments, the second adhesive area 210 comprises a second adhesive or a stronger or different type of adhesive and the second adhesive area 210 comprises the second taggant 320. Thus, a desired pattern or image may be created by the positioning of the second adhesive 210 area having the second taggant 320 on the substrate 180 or the object 170. The type of the second adhesive may be chosen according to the desired signal or image generated by the response wavelength and/or the type of the second taggant 320.

Figure 1C:
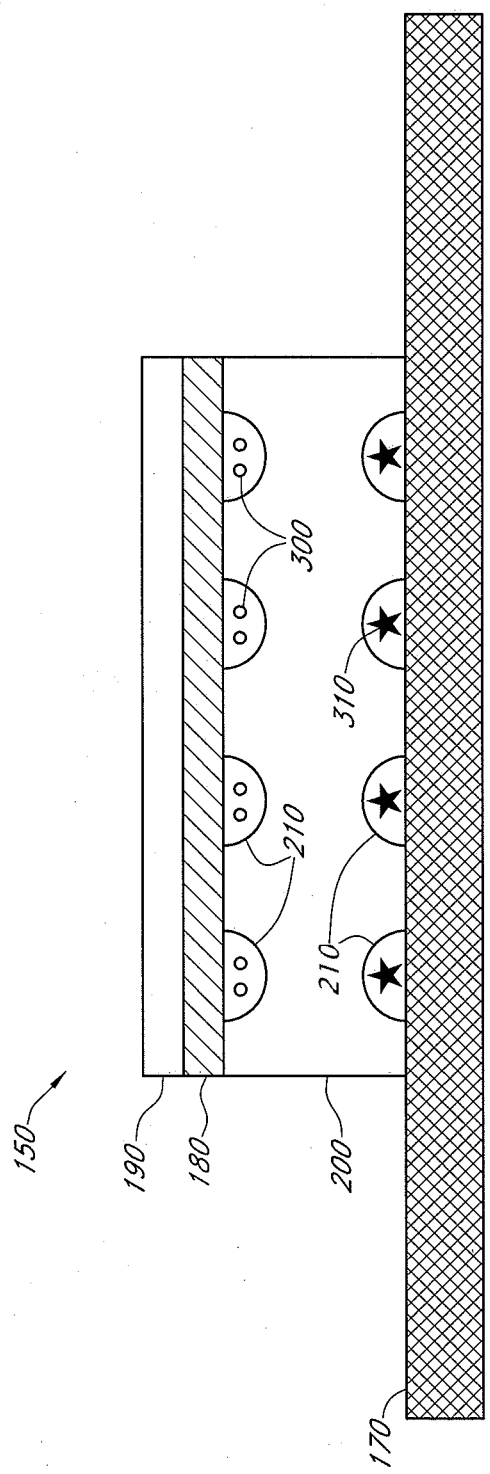
FIG. 1C illustrates a cross-sectional view of one embodiment of an item validation system having specific adhesive areas with taggants.

FIG. 1C depicts an embodiment where the adhesive 200 does not comprise a taggant 300. The adhesive areas 210 are adhered to the substrate 180 and/or the object 170, and may comprise the taggant 300. In some embodiments, the only portion of the label 150 which comprises the taggant 300 is the adhesive areas 210. In some embodiments, the adhesive areas 210 may be disposed only on the substrate 180 of the object 170. The adhesive areas comprising the taggant 300 may be organized or adhered to the substrate 180 to create a desired image, such as a barcode, alphanumeric characters, or any other desired image.

Figure 1D:
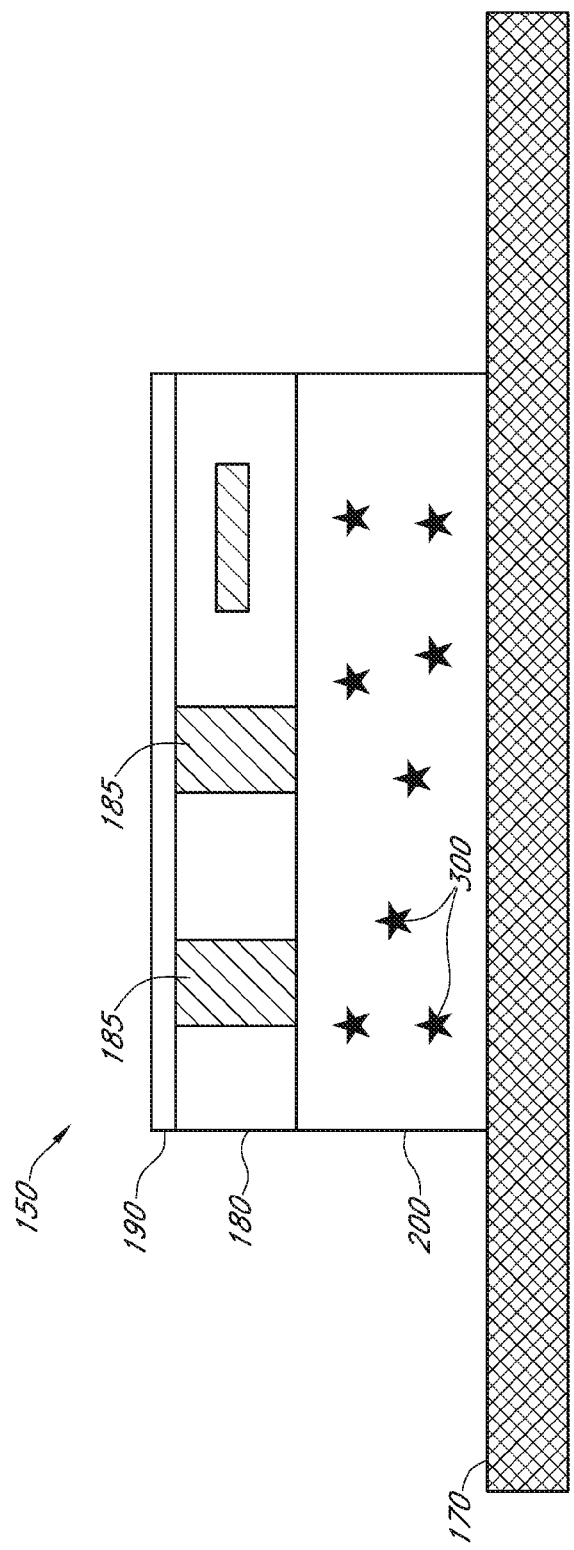
FIG. 1D illustrates a cross-sectional view of an embodiment of an item validation system having embedded portions in a substrate which block a signal emitted from the taggant.

FIG. 1D depicts an embodiment of an item validation system where the taggant 300 acts as a backlight for a security feature, such as a predetermined image. In some embodiments, the label 150 has varying optical properties to impart an image or desired shape or information. To illustrate, the substrate 180 may comprise embedded portions 185. The embedded portions may comprise a material that is opaque to the response wavelength of the taggant 300, or that has a different transmissivity of the response wavelength of the taggant 300. As the interrogation wavelength is applied form the detector, the embedded portions block all or a portion of the response wavelength generated by the taggant 300, and a resulting image or pattern is displayed. In some embodiments, the embedded portion may extend from the adhesive 200 to the top surface of the substrate 180. In some embodiments, the embedded portion 185 may be completely contained within the substrate. In some embodiments, the embedded portion 185 may be invisible to the naked eye, and only detectable when the interrogation wavelength interacts with the taggant 300. In some embodiments, the taggant 300 may be applied to the substrate or printed material 190 or object alone or mixed with a fluid, gel or the like, which may interact with the adhesive and fix the taggant in the shape of the desired image or information.

Taggant Integration with Adhesive

The taggant 300 can be mixed or combined with any type of adhesive 200. In some embodiments, the taggant 300 can be uniformly distributed throughout the adhesive 200. In some embodiments the taggant 300 can be concentrated in a layer within the adhesive 200. With the taggant in the adhesive, removal of the label from the object will destroy the adhesive and remove the taggant from association with the label or strata. In some embodiments in which the adhesive is adhered to a substrate 180, the layer of taggant 300 within the adhesive 200 can be parallel to the substrate 180, perpendicular to the substrate 180, or angularly disposed with respect to the substrate 180. In some embodiments, the taggant 300 can be concentrated in portions of the adhesive 200. In some embodiments, these concentrations can be arranged in a non-random manner. In some embodiments, concentrations of taggant 300 can form image, a pattern, or any shape or combination of shapes. In some embodiments, the image and/or pattern formed by the concentrations of taggant 300 can comprise a code such as, for example, a computer readable code. These computer readable codes can include, for example, a barcode. In some embodiments, the barcode can include, for example, a linear barcode such as a U.P.C. code, a 2D barcode such as, for example, a QR code, or any other barcode. In some embodiments, the concentrations of taggant 300 can form an image. This image can be any image, and can, in some embodiment, include, for example, a logo, a motto, trademark, a decorative image, an indicator of type or class, and indicator of value, or any other desired image.

A variety of mixing operations can be used to mix the taggant 300 with the adhesive 200. In some embodiments, the particles can have a single size, or can comprise a mixture of particles of a variety of sizes. In some embodiments, the distribution of taggant particle sizes can be a normal distribution. In other embodiments, the distribution of taggant particle sizes can be a non-normal distribution. In some embodiments, the taggant particle size distribution can have a median diameter $d_{50}$ of 0.01 µm, 0.1 µm, 1 µm, 2 µn, 5 µm, 10 µm, or any other desired size. In some embodiments the taggant particle size distribution can have a $d_{90}$ of 0.01 µm, 0.1 µm, 1 µm, 2 µn, 5 µm, 6 µm, 10 µm, 20 µm, or any other desired size.

The concentration of taggant 300 found in all or portions of the adhesive layer can vary in different embodiments. In some embodiments, and as discussed above, the concentration of taggant 300 in the adhesive 200 can be uniform or non-uniform. In some embodiments, the concentration of the taggant 300 in regions in which the taggant 300 is intended to be detectable is 2-5% by weight, 1-10% by weight, 1-20% by weight, 1-50% by weight, or any other desired range. In some embodiments, the taggant 300 can be provided to, and added to the adhesives in any desired way. In some embodiments, pure concentrations of taggant 300 can be added to the adhesives 200. In some embodiments, the taggant 300 can be added to the adhesive 200, suspended in a solution. In some embodiments, the taggant 300 can be supplied in an aqueous suspension at 1% solids, 5% solids, 10% solids, 20% solids, 50% solids, or at any other desired concentration. In some embodiments, the properties of the adhesive 200, in combination with the properties of the particles can create a mixture in which the particles quickly or slowly settle. In some embodiments, the taggant 300 may settle in seconds or minutes, and in other embodiments, the taggant 300 may settle in weeks, months, or years. In some embodiments, the taggant 300 can be mixed into the adhesive in a manner that changes the properties of the adhesive 200, or that does not change the properties of the adhesive. In some embodiments, the addition of the taggant 300 to the adhesive 200 does not degrade the adhesive 200 properties.

In some embodiments, the taggant 300 may be imprinted on the back of the label or on a label backing, wherein the adhesive then comes in contact with the taggant 300. In some embodiments, the taggant 300 may be incorporated into a solution or mixture that bonds to or dissolves into the adhesive upon contact with the taggant 300. The mixture of the taggant 300 can simply be the taggant and some adhesive or adhesive precursor. In this way the adhesive then has a localized doping of the taggant 300. This may then impart an image or the like when the taggant 300 is interrogated.

The inclusion of the optical taggant into the adhesive provides added security and increases the ease of use. Adhesives are normally fluid or semi fluid when first mixed/produced. By adding the taggant 300 during adhesive preparation stages when the adhesive is fluid the taggant 300 is easier to mix with the adhesive. Moreover, with the taggant 300 in the adhesive 200 instead of in the label 150 or strata or ink thereof, the removal of the label from an article would destroy or impair counterfeiting by destroying the adhesive. In this way it is more difficult for counterfeiters to remove a genuine label 150 and place it on another article. The substrate 180 also provides some protection to the adhesive. Also, when the taggant 300 is only used in a precursor or the like, as above, the precursor, which is printed on the label or object, would then slightly mix with the adhesive, but the taggant 300 would not migrate throughout the adhesive and would remain only in the area of the printed precursor.

Corresponding Detector

Figure 2:
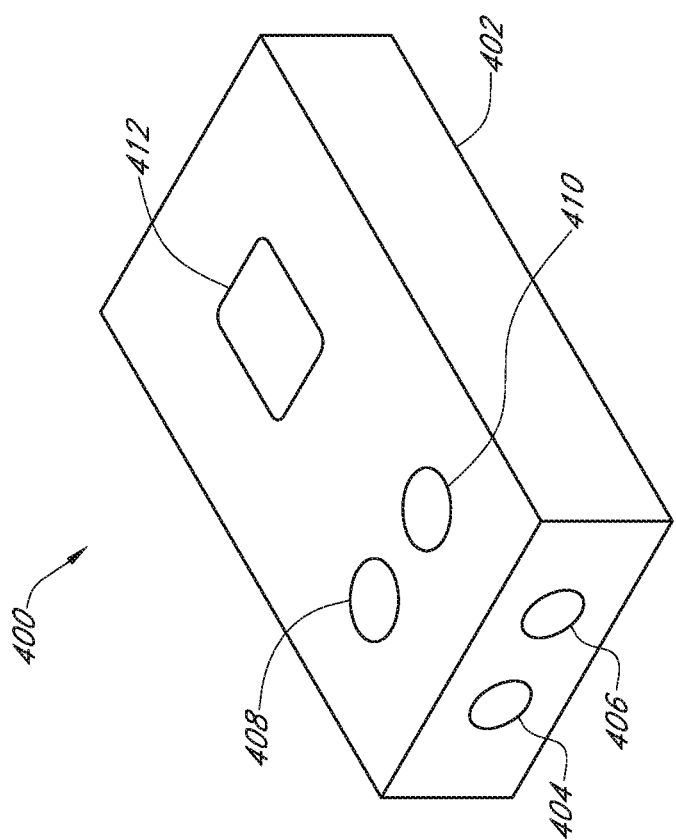
FIG. 2 is a perspective view of an embodiment of a detector for use in item validation.

In some embodiments, the presence of the taggant 300 in the label 150 can be determined by a detector. FIG. 2 illustrates one exemplary embodiment of a detector 400. As depicted in FIG. 2, the detector 400 comprises a body 402. In some embodiments, the body 402 can be configured to define the exterior of the detector 400. The body 402 can be further configured to contain all of the components of the detector. In some embodiments, the body can comprise a natural or a manmade material, and can comprise, for example, metal, plastic, resin, polymer, composite, or any other material.

The detector 400 can include an illuminator 404. The illuminator 404 can comprise any feature configured to emit energy with the desired wavelength. In some embodiments, the illuminator 404 can comprise, for example, a LED, a laser, a light bulb, or any other desired illumination source.

The detector 400 can further include a sensor 406. The sensor 406 can be configured to sense luminescence of excited taggant 300. In some embodiments, the sensor 406 can be configured to sense energy of a specific wavelength, of a specific range of wavelengths, or of any wavelength.

As depicted in FIG. 2, the detector 400 further comprises a first indicator 408 and a second indicator 410. In some embodiments, the indicators can be configured to provide a user of the detector 400 with information relating to the operation, functionality, or any other aspect of the detector 400. In some embodiments, one or both of the first and second indicators 408, 410 can comprise a light, a sound making device, or any other feature capable of providing an identifiable signal to a user. In some embodiments, the first indicator 408 can be configured to indicate when the illuminator 404 is emitting energy. As discussed above, the taggant 300 may be configured for excitation by non-visible light. Accordingly, a user of the detector 400 will not be able to easily determine if the illuminator 404 is emitting energy. This information can be provided to the user by the operation of the first indicator 408.

In some embodiments, the second indicator 410 can be configured to indicate when the detector 400 detects the presence of taggant 300 in an object. In some embodiments, the second indicator 410 can be configured to indicate the presence of a taggant 300 when the sensor 406 detects energy of a required wavelength. As the luminescence may be light in the non-visible spectrum, such a function of the second indicator 410 allows a user of the detector 400 to easily determine the presence or absence of taggant 300 in an object.

As further depicted in FIG. 2, the detector 400 can comprise a control feature 412. In some embodiments, the control feature 412 can be configured to control the operation of the detector 400. In some embodiments, the control feature can be manipulated by the user. In some embodiments, this manipulation can result in the emission of energy from the illuminator 404. In some embodiments, this manipulation of the control feature 412 can result in the operation of the sensor to sense energy of a desired wavelength.

In some embodiments, a detector can further comprise a processor (not shown) and a memory (not shown) comprising stored instructions. The Processor and memory comprising stored instructions can be connected to one or all of the features of the detector 400, and can be configured to send control signals to one or several of the features of the detector 400 and/or to receive information signals from one or several features of the detector 400. Thus, in some embodiments, the sensor 406 can communicate information relating to sensed energy to the processor, and the processor can process this information to determine whether the detected energy indicates the presence of taggant 300 in an object.

A person of skill in the art will recognize that a detector can comprise more features or fewer features than those outlined above. A person of skill in the art will additionally recognize that the detector 400 can provide a user with functionality additional to that described above.

The detector 400 can be configured in a variety of sizes and shapes. In some embodiments, the detector can comprise a stationary device, a mobile device, a handheld device, or a variety of other devices. In some embodiments, the detector 400 can be configured as a handheld device and can be configured to allow a user to carry the detector 400 and use the detector as needed to determine the presence of taggant 300 in an object. The detector 400 can be configured to conduct a simple field test of the authenticity and provide an immediate YES/NO result by, for example, lighting up an indicator and sounding a beep when the taggant 300 is found in a genuine label 150. In some embodiments, IR light from the illuminator may pass through portions of the object to excite the taggant 300, which may allow the detector 400 to detect taggant 300 that is out of line of sight such as, for example, hidden beneath the substrate 180 in adhesive 200.

In some embodiments, the taggant 300 may be able to impart more information than just a YES/NO signal. The layers of the label 150 or of a label may be altered or made to vary the transmissivity of an interrogation or response wavelength, or to vary the reflectance of the interrogation and/or response wavelengths. This may be done by including additives to the taggant 300 such as clays, binders, or other additives with specific optical properties or by varying the density or surface characteristics of the label. Likewise, the optical properties of an ink or imprinted layer on the substrate 180 or in a label may be utilized to absorb or reflect the response or interrogation wavelengths. The inks may be chosen as to appear to the human eye as one color but with different properties for the response or interrogation wavelengths. In this way the information contained in the ink would be hidden except when the detector is used to interrogate the label 150. In some embodiments, the ink may be invisible to the human eye. Binders or other additives may also be used in the label 150 that would block the interrogation or response wavelength in order to show an image from the taggant or the like.

Figure 3:
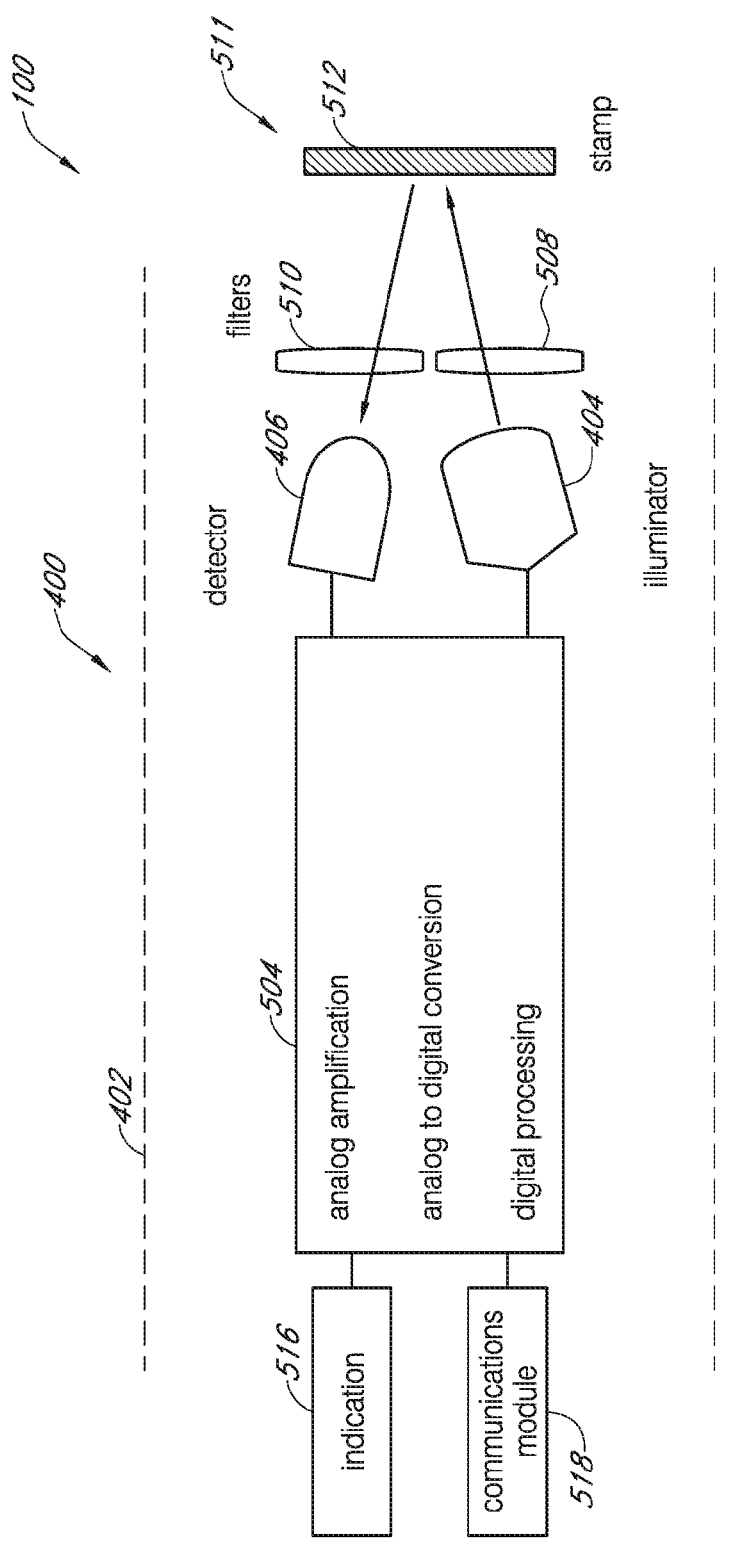
FIG. 3 is a schematic diagram of one embodiment of an authentication system comprising a detector and an object.

FIG. 3 is a schematic illustration of one embodiment of a security system 100 comprising a detector 400 and a taggant bearing item 511. As seen in FIG. 3, the detector comprises the body 402 that is configured to house other components of the detector 400. The body 402 can contain a logic module 504. The logic module 504 can comprise a variety of features, such as, for example, a processor and memory that can include, for example, stored instructions. In some embodiments, the logic module 504 can be configured to communicate with and control other components and/or modules of the detector 400. In some embodiments, the logic module 504 can provide a control signal to initiate illumination of an object, and can receive a sensed signal relating to any luminescence emitted by the object. The logic module 504 can be configured to analyze the sensed signal to determine whether the sensed signal is indicative of the presence of taggant 300 in the object.

The logic module 504 can be configured to perform a variety of functions, such as, for example, analog amplification, analog to digital conversion, digital to analog conversion, and digital processing. In some embodiments, the logic module 504 can be configured to control operation of the detector 400 and communicatingly interact with other components of a system, such as, for example, a delivery system, a transport system, a sorting system, a mail system, or any other desired system.

The logic module 504 can be communicatingly connected with the illuminator 404. As discussed above, the illuminator 404 can be configured to generate the interrogation wavelength, which may comprise electromagnetic energy such as UV, IR, or visible light. The illuminator can be an IR generator, a UV generator, a visible light generator, a microwave generator, or any other generator of energy within the electromagnetic spectrum which is known in the art. In some embodiments, the illuminator 404 can be configured to generate an interrogation wavelength of a single wavelength, a narrow spectrum of electromagnetic energy, or a broad spectrum of electromagnetic energy. In some embodiments, the illuminator 404 can be configured to generate the electromagnetic energy in response to one or several control signals received by the illuminator 404 from the logic module 504.

Electromagnetic energy generated by the illuminator 404 can illuminate an object. In one embodiment, and as depicted in FIG. 3, the object can comprise a taggant bearing item 511, which can comprise, for example, a stamp 512 or other type of postage. In some embodiments, the object can comprise a substrate having an adhesive applied to one or both sides of the substrate, and a taggant at least partially interspersed in the adhesive on one or both sides of the substrate.

In some embodiments, electromagnetic energy generated by the illuminator 404 can directly pass to the stamp 512, and in some embodiments, electromagnetic energy generated by the illuminator 404 can pass through an optical feature before it illuminates the stamp 512. In some embodiments, the optical feature can comprise, for example, a filter, a lens, a mirror, a prism, or any other light affecting feature. In the embodiment illustrated in FIG. 3, the detector 400 comprises a first filter 508. In some embodiments, the first filter 508 can be configured to allow a broad spectrum of electromagnetic energy to pass through the first filter 508, a narrow spectrum of electromagnetic energy to pass through the first filter 508, all electromagnetic energy above a specified wavelength to pass through the first filter 508, all electromagnetic energy below a specified wavelength to pass through the first filter 508, or any other desired selection of electromagnetic energy to pass through the first filter 508.

After the electromagnetic energy impinges on the stamp 512, the taggant 300 generates a response wavelength, or, in other words, electromagnetic energy is emitted or reflected from the stamp 512 and the surroundings is sensed by the sensor 406. In some embodiments, electromagnetic energy can directly travel to the sensor 406, and in some embodiments, electromagnetic energy can pass through an optical feature before it reaches the sensor 406. In some embodiments, the optical feature can comprise, for example, a filter, a lens, a mirror, a prism, or any other light affecting feature. As depicted in FIG. 3, the detector 400 comprises a second filter 510. In some embodiments, the second filter 510 can be configured to allow a broad spectrum of electromagnetic energy to pass through the second filter 510, a narrow spectrum of electromagnetic energy to pass through the second filter 510, all electromagnetic energy above a specified wavelength to pass through the second filter 510, all electromagnetic energy below a specified wavelength to pass through the second filter 510, or any other desired selection of electromagnetic energy to pass through the second filter 510.

As depicted in FIG. 3, the sensor 406, which is communicatingly connected with the logic module 504, can sense electromagnetic energy of the response wavelength and can communicate a sensed signal to the logic module. The logic module 504 can receive and analyze the sensed signal to determine whether the illuminated object contains taggant 300, and thereby authenticate the illuminated object.

As further depicted in FIG. 3, the logic module 504 can be communicatingly connected with an indication module 516. In some embodiments, the indication module 516 can comprise a variety of features and perform a variety of functions. In some embodiments, the indication module 516 can comprise one or several indicators, that can comprise features configured to provide an indication of the functionality of the detector and the results of the object illumination to a user or to another system entity, such as, for example, a server, a processor, or any other system component. As discussed above, in some embodiments, an indicator can comprise features, such as, for example, a light or a sound making device. In some embodiments, an indicator can comprise features such as, a display or a monitor, or any other feature capable of communicating information to a user or other system entity.

As further depicted in FIG. 3, the detector 400 can further comprise a communications module 518 that can be communicatingly connected to the logic module 504. In some embodiments, the communications module 518 can be configured to communicate with other system entities, such as, for example, a server, a processor, or any other system component. In some embodiments, the communications module 518 can be configured for wired or wireless communications. In some embodiments, the communications module 518 can be configured to introduce dynamic changes to a system in the event that an object is or is not authenticated. In some embodiments, for example, in which a plurality of objects are passed through a system for authentication, the communications module 518 can be configured to communicate information relating to the authenticity of the object, which information can be used to segregate the authenticated objects from the non-authenticated object.

In some embodiments, the detector 400 can additionally comprise an interlock (not shown). The interlock can be configured, for example, to help prevent the detector 400 from harming its operator or damaging itself by stopping the detector 400 when tripped. A person of skill in the art will recognize that a variety of different interlocks can be incorporated into the detector 400.

A person of skill in the art will recognize that the detector can comprise more or fewer features, components, and/or modules than those outlined above. A person of skill in the art will likewise recognize that the detector discussed above with respect to FIGS. 2 and 3 can be used in a variety of functions and as a stand-alone device, or as an integral system component.

Figure 4:
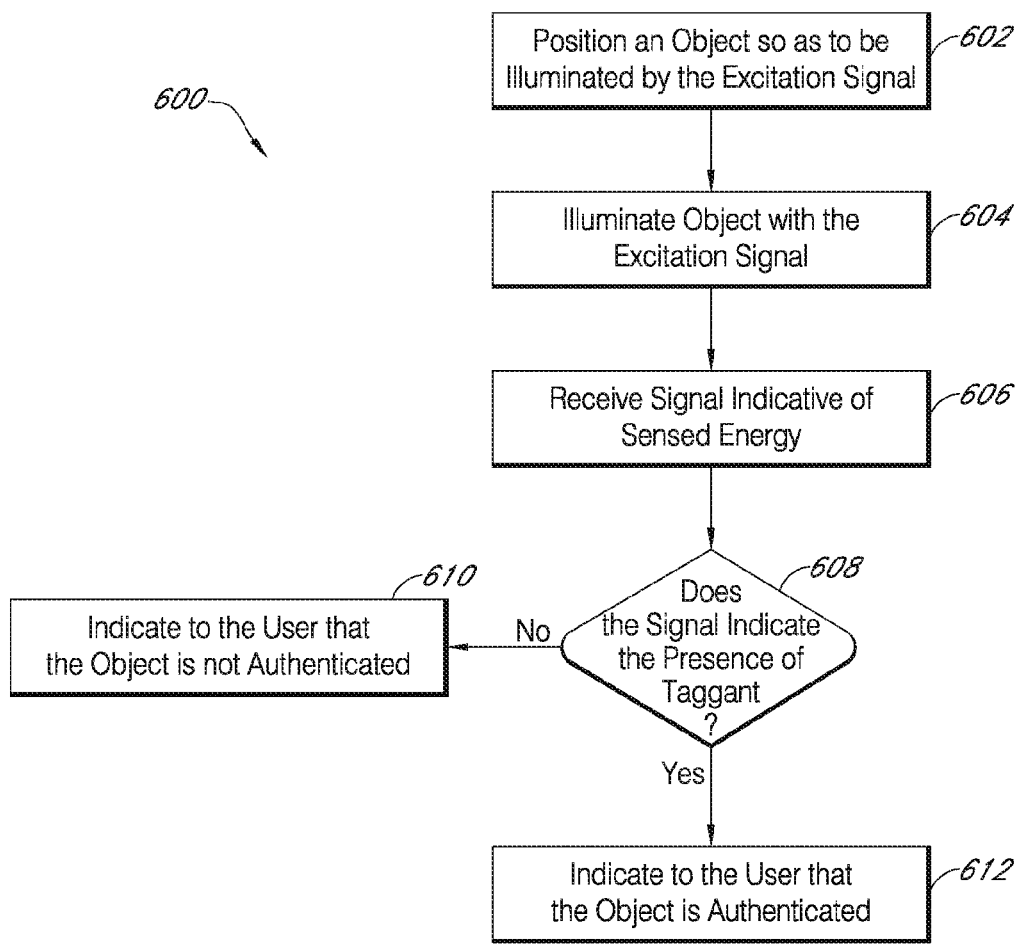
FIG. 4 is a flow-chart illustrating an embodiment of a process for authenticating an item via luminescent taggants.

FIG. 4 is a flow-chart illustrating one embodiment of the authentication process 600 accomplished by the detector. As depicted in FIG. 4, an process 600 begins at block 602 and the object is positioned so as to be illuminated by the excitation signal. In some embodiments, the illuminator 404 may have an effective illumination range. In some embodiments this range may be, for example, less than one inch, less than three inches, less than six inches, less than one foot, less than ten feet, or any other desired range. In some embodiments, the object will be positioned so as to be illuminated by the excitation signal as depicted in block 602 and the object will be positioned within the effective illumination range of the illuminator 404.

The process 600 then proceeds to block 604 and the object is illuminated with the excitation signal. As discussed above, the illumination of the object may be controlled by the control feature 412.

After the object is illuminated with the excitation signal in block 604, the process 600 moves to block 606 and receives a signal indicative of sensed energy. In some embodiments, this signal originates at the sensor 406 and is received by the processor or the logic module 504 of the detector 400.

After the signal indicative of sensed energy is received in block 606, the process moves to decision state 608 and determines if the signal indicates the presence of taggant 300. As discussed above, the taggant 300 can be configured to emit energy of a designated frequency in response to its illumination and excitation by the excitation signal. Thus, in some embodiments, the detector 400 can be configured to determine if energy of a designated wavelength is detected. In some embodiments, and as discussed above, the taggant 300 can emit energy for the duration of the illumination, or for a period of time beyond the time of illumination. In some embodiments, the detector 400 can use the decay of emitted energy to authenticate the object.

If the signal does not indicate the presence of taggant 300, then the process 600 moves to block 610 and indicates to the user that the object is not authenticated. If the signal does indicate the presence of taggant 300, then the process 600 moves to block 612 and indicates to the user that the object is authenticated.

Figure 5:
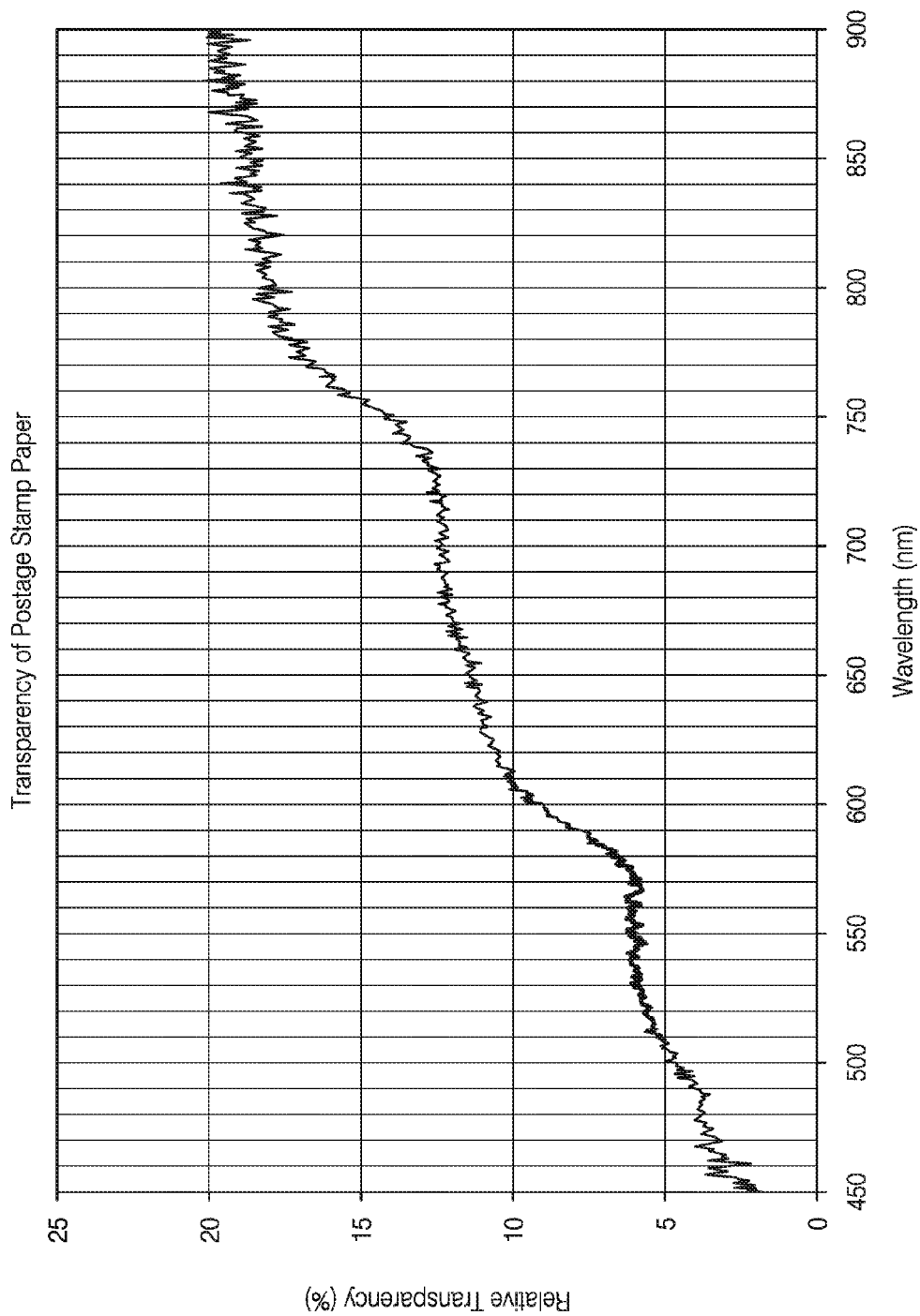
FIG. 5 is a graphical illustration of variation in the transparency of a substrate for light of different wavelengths.

In some embodiments, the label 150 can be configured and arranged so that the energy illuminating the taggant 300 must pass through the substrate 180 before it is incident upon the taggant 300. Similarly, in some embodiments the energy emitted from the taggant 300 must pass through the substrate 180 before it can be sensed by the detector 400. Advantageously, many types of thin substrates 180, and even thin substrates 180 of other materials, such as wood, allow energy of certain wavelengths to pass. FIG. 5 is a graph illustrating the relative transparency as a percent of postage stamp paper for energy of certain wavelengths. As seen in FIG. 5, as the wavelength of the energy increases, the postage stamp paper becomes relatively more transparent. Thus, energy of higher wavelengths can more readily pass through postage stamp paper. Thus, in an embodiment in which the excitation signal must pass through postage stamp paper before it is incident upon taggant located in adhesive found on the back of the postage stamp paper, excitation and emission signals will be better able to pass through the postage stamp paper as their wavelengths increase.

In some embodiments in which the taggant 300 is located on an item so that the excitation signal and the emitted signal must pass through portions of the item before they are incident upon the taggant 300 or the detector 400 respectively, the relative transparency of portions of the object can be determined to determine optimal frequencies of the excitation signal and of the emitted energy to allow detection of the taggant 300.

Figure 6:
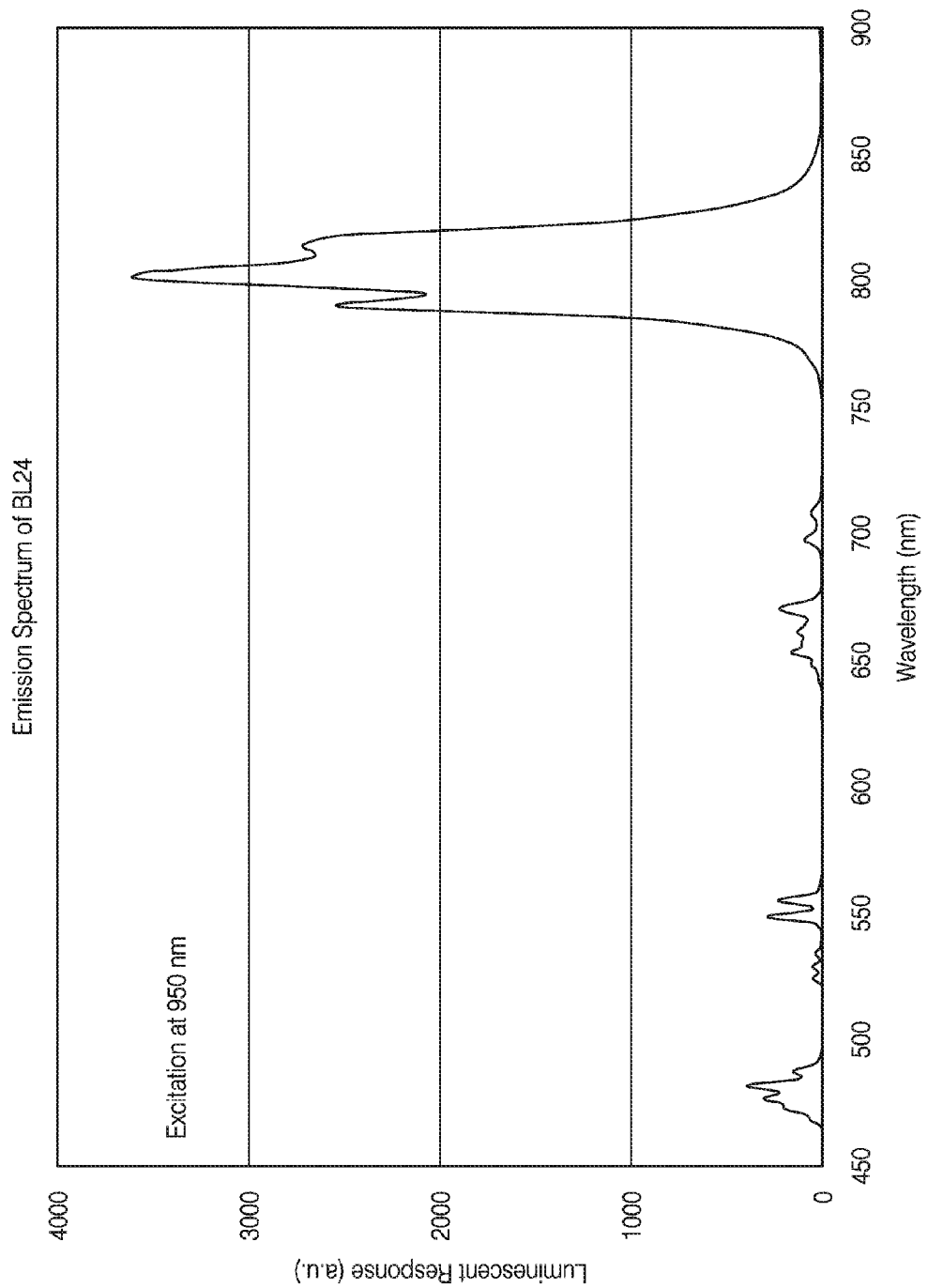
FIG. 6 is a graph illustrating the optical pigment BL24 emitting luminescence in a series of narrow spectral peaks around 800 nm while subjected to excitation at 950 nm.

In some embodiments, the relative transparency of a substrate 180 can be used to select an optical pigment to allow the maximum amount of the excitation signal to pass to the taggant 300 and to allow the maximum amount of the emitted energy to pass to the detector 400. FIG. 6 depicts a chart illustrating the luminescence spectrum of an optical pigment BL24 in response to excitation by electromagnetic radiation having a wavelength of 950 nm. As depicted in FIG. 6, BL24 emits luminescence in a series of narrow spectral peaks, with the largest occurring around 800 nm. Due to the combination of the large wavelength for the excitation energy of BL24 and the large wavelength for the luminescence of BL24 that is so stimulated, BL24 is well suited for use with a postage stamp paper having the properties depicted in FIG. 5.

Thus, in some embodiments, the substrate 180, the taggant 300, and the frequency of the excitation signal of the detector 400 can be selected to facilitate authentication of an item. Thus, in some embodiments, the properties of the substrate 180 can be determined, and based on the relative transparency of the substrate 180, a desired range of excitation signal wavelengths and emitted luminescence wavelengths can be selected. In some embodiments, these desired ranges can be used to select the appropriate taggant 300.

In some embodiments, the taggant 300 can be selected. The taggant 300 can be evaluated to determine its optimal excitation wavelengths and its emitted luminescence wavelengths. Based on this taggant information, the substrate can be selected, or the properties of the substrate 180 can be manipulated to better correspond to the taggant properties.

Use in a Stamp

As discussed above, some embodiments can involve the use of a substrate 180 having an adhesive 200 on one or more of the sides of the substrate 180. As further discussed above, in some embodiments, the taggant 300 can be generally or selectively interspersed through all or portions of the adhesive 200. In one embodiment, the substrate 180 can comprise a stamp and the adhesive 200 can comprise a stock adhesive. In some embodiments, the stamp can comprise a printed coating that can depict to value of the stamp, a decorative image, a logo, or any other desired image. In one embodiment in which the taggant 300 is used in one or several stamps, or any other object that is exposed to environmental factors, the taggant 300 can be resistant to environmental factors and can be, for example, resistant to the effects of direct or indirect sunlight, to temperature and temperature variations, to humidity, and/or any other environmental factors. Additionally, in some embodiments in which the taggant 300 is used in a stamp or other item in which the appearance of the item is important, the taggant 300 have a low loading in the item, which low loading can prevent changes in the appearance of the printed coating.

In some embodiments, and as discussed above, the taggant 300 can be applied to the adhesive 200, and can thereby be concealed from the human eye. In some embodiments, the properties of the substrate 180 can be optimized with properties of the taggant 300 and the electromagnetic energy used by the detector 400 to allow electromagnetic energy to pass through the substrate 180 to excite the concealed taggant 300.

Further, in some embodiments, the integral manufacture of the adhesive 200, including the taggant 300, and the substrate 180 can provide a security feature that cannot be removed from the substrate 180 with the intention of re-using the feature. Further, due to the different detector configurations, the system 100 provides flexibility in authentication of postage stamps and other stamp products both in-line at sort facilities and out in the field through utilizing different designs of the authenticating apparatus.

Other advantages of the system 100 include that fact that the taggant-impregnated components of the item, such as the stamp, retain their design appearance. For example, an inspector can find and authenticate the product's security feature effortlessly. The life time of the protection is practically unlimited. The taggant 300 in the stamp is not degraded by handling, humidity, storage temperature, or direct sunlight. The manufacturing process of the stamp components is not made any more complex or expensive by adding the taggant 300 to them. The taggant 300 also includes a forensic ("court-admissible") level of security. The development provides for a single, exclusive, covert solution that can be applied to different stamps. The solution is quite inexpensive while, in one embodiment, the detectors may be supplied free of charge.

Embodiments of the development may also be used in a variety of applications, such a stamp, an address label, or other labels. It will be understood by those of skill in the art that numerous and various modifications can be made without departing from the spirit of the development. Therefore, it should be clearly understood that the forms of the development described herein are illustrative only and are not intended to limit the scope of the development.

Customization

Some embodiments relate to methods of customizing an item. As referred to herein, "customize" and "customized" refer to one or more graphic features received from a requester or items containing such features. As referred to herein, "non-customized" and "generic" refer one or more graphic features applied generally to the class of items such as, for example, a value indication, class indication, or source indication applied to a stamp. In some embodiments, and as discussed above an item can comprise printed material 190. In some embodiments, the printed material can include information designating the item or a characteristic of the item, such as, for example, a class, issuer, or value of the item. In some embodiments, the printed material 190 can further include a graphic. In some embodiments the graphic can comprise a computer readable code, information such as, for example, a trademark, a message, or a decorative image.

Figure 7:
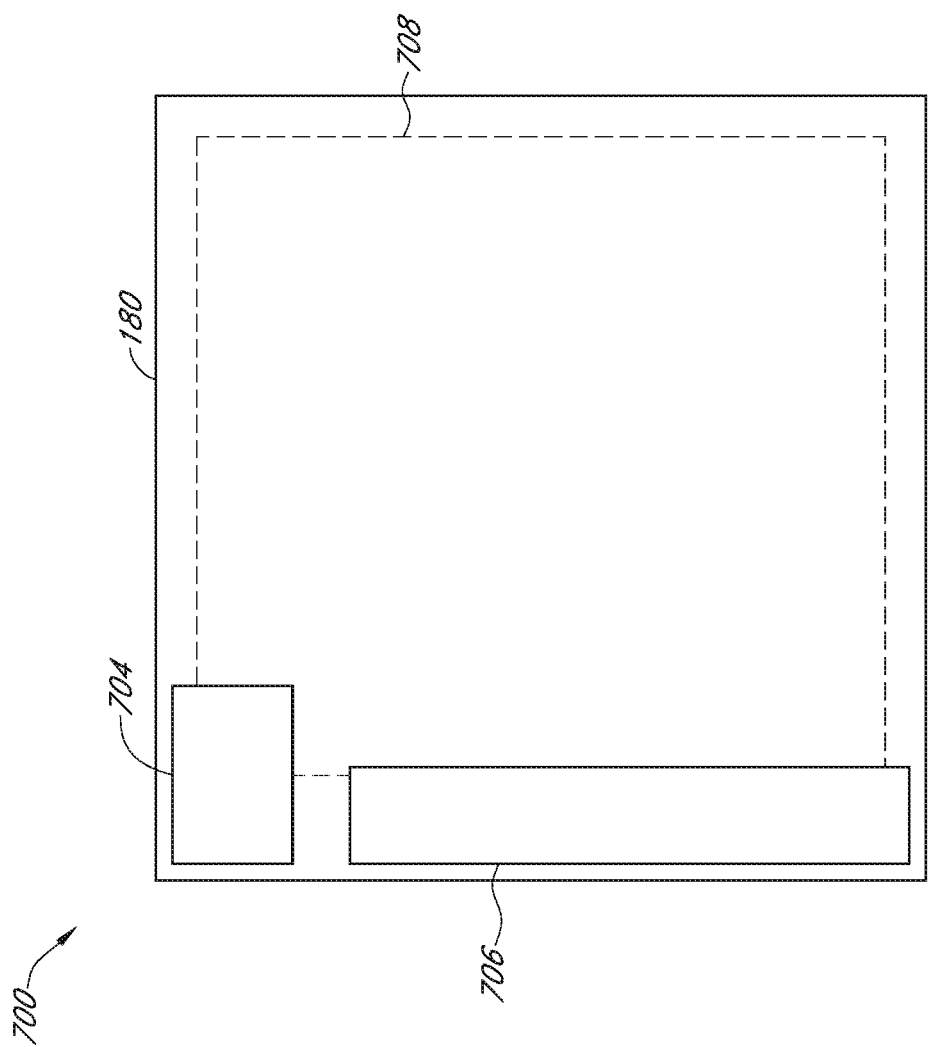
FIG. 7 is a schematic illustration of one embodiment of a label having a first and a second information area.

In one specific embodiment, the item can be any desired item. In some embodiments, the item can comprise any dual use item capable of a first function, and a second decorative function, including, for example, a postage stamp, a check, an I.D., and a license plate. FIG. 7 depicts one embodiment of an label 700. In one embodiment, the label 700 can comprise a substrate 180, a first information area 704, a second information area 706, and a graphic area 708. In some embodiments, the label 700 can comprise additional or fewer information areas 704, 706, and/or graphic areas 708.

In some embodiments, the substrate 180 can comprise a variety of materials and can be configured in a variety of shapes and sizes. In some embodiments, for example, the substrate 180 can comprise, for example, sheet metal, paper, plastic, wood, metal, composites, a natural material, a man-made material, or any other desired material. In some embodiments, the substrate 180 can be configured for functionality in the environment in which it will be used. Thus, in some embodiments, a substrate 180 for use as license plate can comprise a material capable of resisting the elements to which a license plate is exposed, such as, for example, galvanized steel sheet metal. Similarly, a substrate 180 for use as a postage stamp can comprise paper, or a specific type of paper capable of resisting the elements to which a postage stamp is exposed. As mentioned, a substrate 180 can comprise any desired size and shape.

As mentioned, the label 700 can comprise the first information area 704 and the second information area 706 and can additionally comprise further or fewer information areas. The information areas 704, 706 can comprise the portion of the label 700 containing an item or information relevant to the first function of the label 700. In some embodiments, this item or information can include, for example, an identification feature such as an identification number or a computer readable code, a class indicator, a value indicator, a trademark or logo, a security feature, or any other item or information relevant to the first function of the label 700. In one specific embodiment in which the label 700 is a postage stamp, the first information area 704 can comprise, for example, an indicator of the stamp value, and the second information area 706 can comprise, for example, an indicator of the stamp class or service associated with the stamp.

The label 700 can comprise the graphic area 708. As discussed above, some embodiments, of the label 700 can comprise additional graphic areas. Further, different embodiments of the label 700 can comprise graphic areas of different sizes and shapes. In some embodiments, the graphic area 708 can roughly comprise the size and shape of the label 700, and in other embodiments, the size and shape of the graphic are 708 can be different than the size and shape of the label 700.

The graphic area 708 can be configured to display a graphic relevant to the decorative use of the label 700. In some embodiments, the graphic can comprise any desired graphic, including, text such as, for example one or several number, symbols, or letters, a computer readable code, an image, or any other desired graphic.

Figure 8:
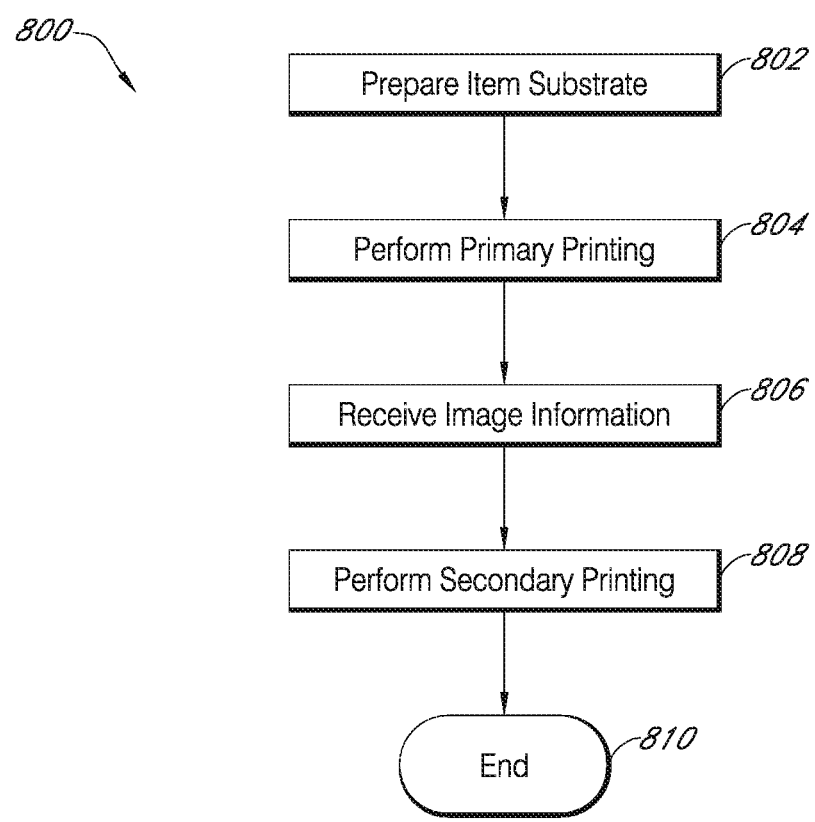
FIG. 8 is a flow-chart illustrating an embodiment of a process of making a label.

FIG. 8 is a flow-chart illustrating one embodiment of a process 800 of making the label 700. In some embodiments, the process 800 begins in block 802 and the item substrate 180 is prepared. In some embodiments, the preparation of the item substrate 180 can comprise any steps to prepare the item substrate 180 for further processing. In some embodiments this step can include, treating the substrate 180, such as, for example, applying an adhesive to the substrate 180, applying chemicals such as, for example, a chemical primer to the substrate 180, cutting the substrate 180 to the desired size, perforating the substrate 180 into easily dividable sections, or any other preparatory step.

After the label substrate 180 is prepared in block 802, the process 800 continues to block 804 and performs the primary printing. In some embodiments, the primary printing can comprise adding material to one or both of the first and second information areas 704, 706 to the substrate 180. In some embodiments, this application can comprise printing the material on the first and second information areas 704, 706 of the substrate 180, or using any other desired method to add desired material to the first and second information areas 704, 706 of the substrate 180. In some embodiments, this step can comprise adding material to more or fewer information areas found on the substrate 180.

In some embodiments, the information added to the first and second information areas 704, 706 can comprise, for example, item information relating to the assigned value of the item, to the type of goods with which the item will be associated, to the source of the item, to the class of goods designated by the item, or to any other desired information. In some embodiments, the information added to the first and second information areas 704, 706 can comprise a background pattern or decorative features. In some embodiments, the information can comprise generic, non-customized information.

After the primary printing is performed in block 804, the process 800 moves to block 806 to receive image information. In some embodiments, the receipt of image information can comprise the receipt of a hard-copy of an image, pattern, or any other graphic that should be added to the substrate 180. In some embodiments, the receipt of image information can comprise the receipt of a digital or soft-copy of an image, pattern, or any other graphic that should be added to the substrate 180. In some embodiments, the image information can be received via an electronic communication, such as via an email, an internet transmission, an SMS, a fax, or any other form of electronic communication. In some embodiments, the image information can be received via a personal delivery, via a mail delivery, via a courier, or via any other desired delivery or transport form.

In some embodiments, the received image information can be processed to determine the acceptability of the received image information. In some embodiments in which the image information comprises digital information, the determination of acceptability of the received image information can comprise evaluating the received information for malware such as, for example, a virus, a cookie, or any other potentially harmful software. In some embodiments, the determination of the acceptability of the received image information can relate to determining the acceptability of the image content, i.e. determining that the image information is not pornographic, the acceptability of the image quality, the acceptability of the image format, or any other desired determination.

After the image information has been received in block 806, the process 800 moves to block 808 and performs secondary printing. In some embodiments, the secondary printing can comprise adding material to the graphic area 708 of the substrate 180. In some embodiments, this application can comprise printing the material on the graphic area 708 of the substrate 180, or using any other desired method to add desired material to the graphic area 708 of the substrate 180. In some embodiments, this step can comprise adding material to more or fewer graphic areas found on the substrate 180.

After the secondary printing has been performed in block 808, the process 800 terminates at block 810. A person of skill in the art will recognize that a process 800 of making the label 700 can include some or all of the above discussed steps, as well as steps additional to the above requested steps. A person of skill in the art will further recognize that process 800 of making the label 700 can include the above listed steps performed in any order, including in an order different than that shown above.

Figure 9:
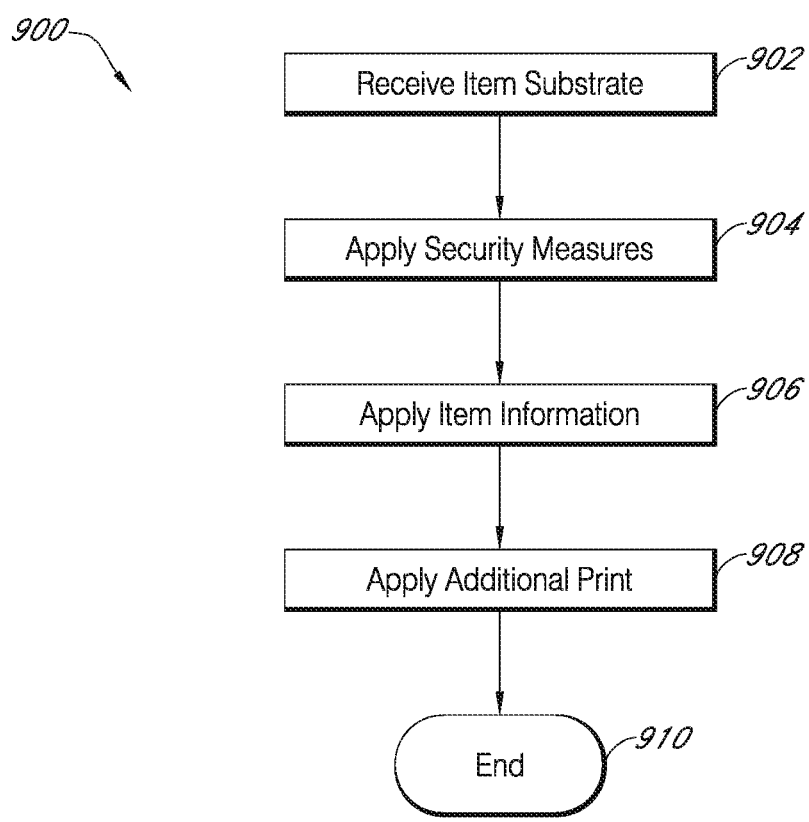
FIG. 9 is a flow-chart illustrating an embodiment of a process of performing the primary printing.

FIG. 9 is a flow-chart illustrating one embodiment of a process 900 of performing the primary printing as is accomplished in the process of block 804 of FIG. 8. The process 900 begins at block 902 and receives the item substrate. After receiving the item substrate at block 902, the process moves to block 904 and applies security measures. The security measures can comprise a variety of features. In some embodiments, the security features can comprise a printed feature, a feature integrated into the substrate 180, a feature applied to the substrate, or any other feature. In some embodiments, the security feature can comprise a microprint, a watermark, a graphic printed with UV, phosphor, or other special ink. In some embodiments, the security feature can comprise, for example, a phosphor tag. In some embodiments, the security feature can comprise a feature integrated into the substrate 180 such as, for example, threads, a security strip, a tag such as, for example, a RFID tag, or any other feature. In some embodiments, the security feature can comprise a feature applied to the substrate 180, such as the taggant 300 described above, or any other desired feature.

After the security measures are applied to the substrate 180 as described in block 904, the process 900 moves to block 906 and applies item information to the substrate 180. In some embodiments, the item information can comprise information relating to the non-customized item such as, for example, an identification feature such as an identification number or a computer readable code, a class indicator, a value indicator, a trademark or logo, a security feature, or any other item or information relevant to the first function of the label 700. In one specific embodiment in which the label 700 is a postage stamp, the item information can comprise, for example, an indicator of the stamp value and an indicator of the stamp class or service associated with the stamp.

After the item information is applied to the substrate 180 in block 906, the process 900 moves to block 908 and applies additional print. In some embodiments, the additional print can comprise further non-customized graphical information, such as, for example, a background pattern, a border pattern, a color scheme, or any other generic graphic.

After any additional print is applied in block 908, the process 900 terminates at block 910. A person of skill in the art will recognize that a process 900 of performing the primary printing can include some or all of the above discussed steps, as well as steps additional to the above requested steps. A person of skill in the art will further recognize that process 900 of performing the primary printing can include the above listed steps performed in any order, including in an order different than that shown above.

Figure 10:
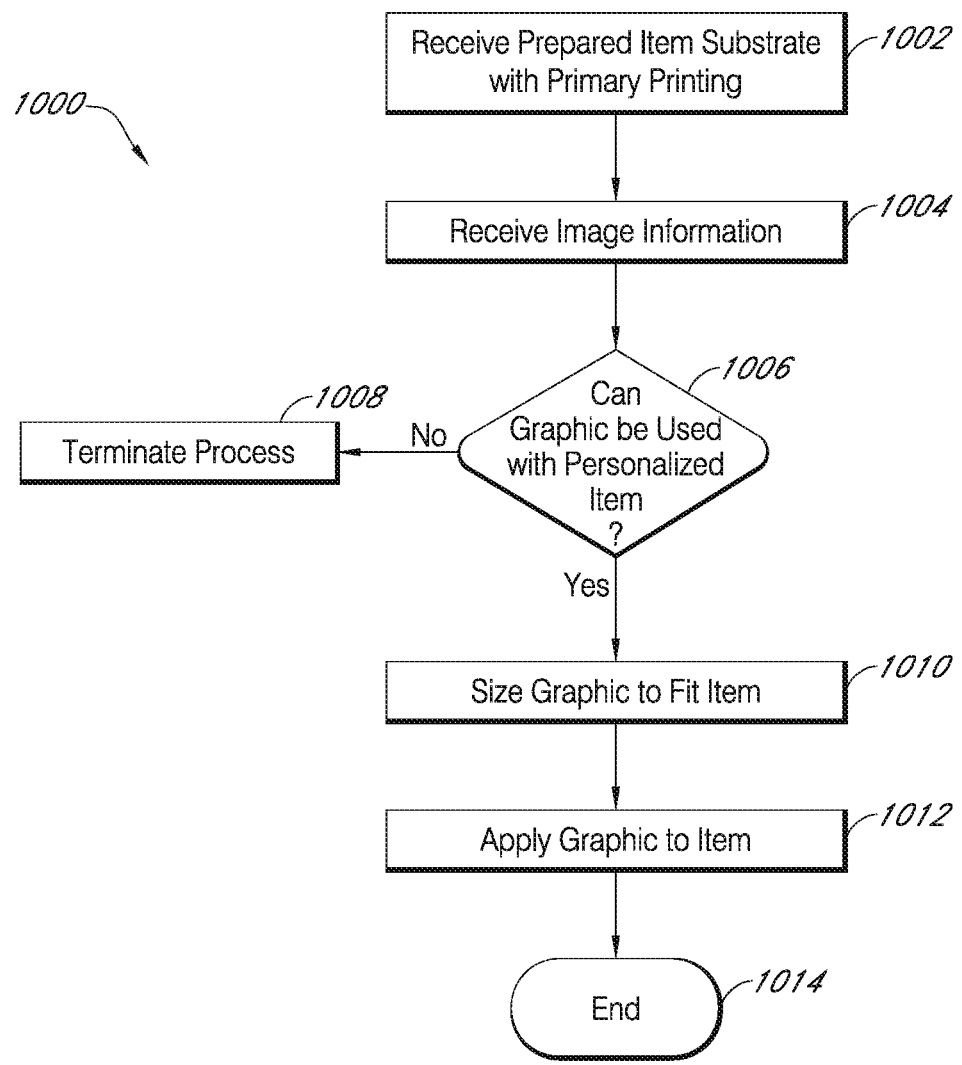
FIG. 10 is a flow-chart illustrating an embodiment of a process of receiving the image information and performing the secondary printing.

FIG. 10 is a flow-chart illustrating one embodiment of a process 1000 of receiving the image information and performing the secondary printing, as is performed in the process of blocks 806 and 808 of FIG. 8. The process 1000 begins in block 1002 and receives the prepared item substrate with the primary printing. In some embodiments, the item substrate can be prepared and the primary printing can be performed as described above.

After the process 1000 receives the prepared item substrate with the primary printing, the process 1000 moves to block 1004 and receives the image information. As discussed above, the image information can relate to any desired graphic, and can include, for example, text, characters, a computer readable code, a decorative image, or any other graphic. The image information can further comprise any desired format. In some embodiments, the image information can comprise a hard-copy of a graphic. In some embodiments this hard-copy can comprise, for example, a photograph, a drawing, a painting, a sketch, or any other physical copy of a graphic. In some embodiments, the image information can comprise a soft-copy of a graphic, including data comprising, for example, a digital graphic, a digital image, a digital photograph, a digital painting, a digital sketch, or any other digitized graphic.

After the process 1000 receives the image information at block 1004, the process 1000 moves to decision state 1006 and determines if the graphic can be used with a personalized item. In some embodiments, this determination comprises determining whether the physical characteristics of the received graphic information comply with requirements for the image information. This can include, for example, an evaluation of the image information to determine if quality, size, and content requirements for the image are met. In some embodiments, this can include refusing certain content, such as pornographic, crude, or otherwise undesired content. In some embodiments this can include refusing certain images, including graphics that are too large, too small, have too many colors, have too high or too low resolution, or that fail to meet any other image information criteria.

If the process 1000 determines that the graphic cannot be used with the personalized item in block 1006, then the process 1000 moves to block 1008 and the process 1000 terminates.

If the process 1000 determines at decision state 1006 that the graphic can be used with the personalized item, then the process 1000 moves to block 1010 and the graphic is sized to fit the item. In some embodiments this can comprise shrinking or blowing-up the graphic to fit the item. In some embodiments, sizing the graphic to fit the item can comprise adjusting the shape of the graphic by, for example, compressing and/or stretching the graphic in one or several directions. In some embodiments, sizing the graphic to fit the item can comprise adjusting the shape of the graphic by, for example, truncating or trimming portions of the graphic.

After the graphic has been sized to fit the item in block 1010, the process 1000 moves to block 1012 and applies the graphic to the item. The graphic can be applied to the item using a variety of techniques. In some embodiments, the graphic can be printed on the item, embossed on the item, transferred to the item, or applied to the item using any other desired technique. In some embodiments, the graphic can be applied serially to a plurality of items, and in some embodiments, the graphic can be applied simultaneously to a plurality of items. In some embodiments, the graphic can be applied both serially and simultaneously to a plurality of items.

After the graphic has been applied to the item in block 1012, the process 1000 terminates at block 1014. A person of skill in the art will recognize that a process 1000 of receiving the image information and performing the secondary printing can include some or all of the above discussed steps, as well as steps additional to the above requested steps. A person of skill in the art will further recognize that process 1000 of receiving the image information and performing the secondary printing can include the above listed steps performed in any order, including in an order different than that shown above.

In some embodiments, the primary and secondary printing can comprise temporally separated steps, and in some embodiments, the primary and secondary printing can comprise simultaneously performed steps. In some embodiments, the primary and secondary printings can be performed at the same location on the same equipment. In some embodiments, the primary and secondary printings can be performed at different locations and by different equipment. In some embodiments, the item substrates can be packaged after the primary printing. In some embodiments, the item substrates can be removed from the packaging before the secondary printing. In some embodiments, the packaged substrates can be sold to a customer who can, for example, perform the secondary printing.

Figures 11, 12:
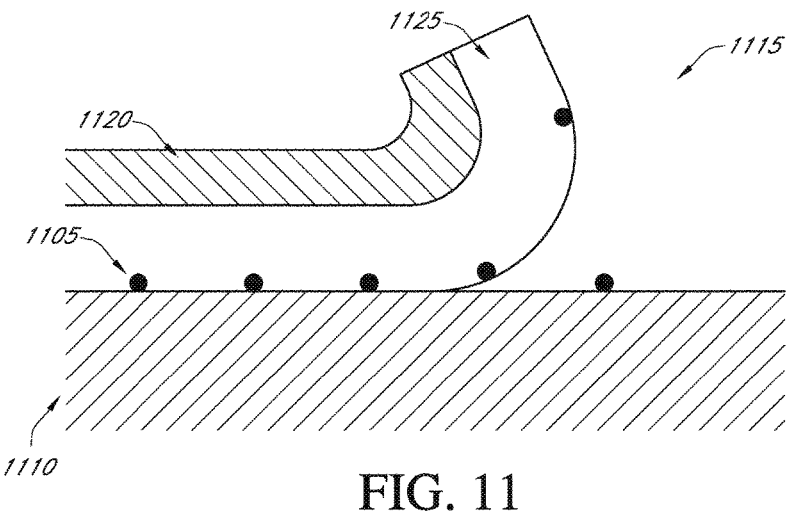
FIG. 11 is a cross sectional view of another embodiment of an authentication system having a portion of a taggant selectively adhering to the adhesive.
FIG. 12 depicts another embodiment of an item validation system having a matrix of authentication cells.

FIG. 11 depicts one embodiment of an authentication system. In an embodiment, a taggant 1105 may be printed on an object 1110. In some embodiments, the object 1110 may be a backing or other surface on which a label, stamp, or other item may be located. The taggant 1105 may be screened, painted, deposited, sprayed, printed or otherwise placed on the object 1110 in a first pattern. The first pattern can be a recognizable image or can be a uniform or random distribution of taggant. In some embodiments, the taggant 1105 can be placed on the object in a particular or first pattern to form or create an image, an alphanumeric code, a computer readable code, or other desired pattern. A label 1115, which includes a substrate 1120 and an adhesive 1125 may be disposed or placed on the object 1110. For example, the label 1115 may be a postage stamp which is placed on to the object 1110, which could be a backing.

When the label 1115 is placed or located on the object 1110, the adhesive 1125 contacts the object 110 and the taggant 1105 located thereon. All, some, or none of the taggants 1105 printed on the object may dissolve into the adhesive 1125, mix into the adhesive 1125, diffuse into the adhesive 1125, become attached to the adhesive 1125, or otherwise combine with the adhesive 1125. When the label 1115 is peeled off of the object 1110, all, some, or none of the taggant 1105 will adhere to the adhesive 1125, and may be peeled off with the label 1115, with all, some, or none of the taggant 1105 remaining on the object. The taggant which peels off with the label may comprise a second pattern. the second pattern can correspond to a specific image, such as a computer readable code, an image, an alphanumeric code, and the like. In some embodiments, the second pattern is different from the first pattern.

In some embodiments, a user may influence the behavior of the taggant 1105 with regard to the adhesive 1125 in a variety of ways. For example, a user may irradiate and/or illuminate a taggant 1105 with light of different wavelengths. For example, as described elsewhere herein, the taggant 1105 may be configured to emit a certain wavelength upon excitation with electromagnetic energy. In some embodiments, the taggant 1105 may be configured to emit energy when excited with light having a certain wavelength. The taggant 1105 can be selectively adhered to the adhesive 1125 based on this effect in order to create the second pattern of taggant in the adhesive. For example, when electromagnetic energy having a specific wavelength excites the taggant 1105, or when the taggant 1105 emits a specific wavelength, this can cause a taggant 1105 to detach from an object 1110 to mix or dissolve into an adhesive 1125. In this way, a user may place the label 1115 onto the object 1110, irradiate the label 1115 with electromagnetic energy to control which portions of the pattern of the taggant 1105 are peeled off with the label 1115. In some embodiments, the electromagnetic energy with which the label 1115 is irradiated may be applied in a particular, predetermined pattern such that a predetermined pattern of the taggant 1105 is formed.

In some embodiments, the distribution of the taggant 1105 into the adhesive 1125 can be determined or controlled based on contact with different types of adhesive 1125. For example, certain types of taggant 1105 may dissolve or mix more readily into a certain type of adhesive 1125 and other types of taggant 1105 may not. The adhesive 1125 can include layers or patterns of different types of adhesive. For example, a first adhesive can be applied to the substrate 1120 in a specific pattern and a second adhesive can be applied to the substrate 1120 in a complementary or overlapping pattern. In some embodiments, the first adhesive can be applied to an entire surface of the substrate 1120, and a second adhesive can be applied to the first adhesive in a specific pattern. As the label 1115 is affixed or placed on the object 1110, the specific pattern of the first and/or second adhesive can have different adhesive capabilities with regard to the one or more types of taggant 1105 on the object 1110, thereby forming a predetermined pattern of the taggant 1105 when the label 1115 is removed from the object 1110. In this way, a user may also control which taggants 1105 are peeled off with a label by selecting a particular type of taggant 1105 and/or adhesive 1125.

In some embodiments, the adhesive 1125 may be a photocurable adhesive, UV curable adhesive, or other type of adhesive that cures to an extent when irradiated by electromagnetic energy. In some embodiments, the taggant 1105 can be randomly or uniformly distributed on the object 1110. With the label 1115 on the object 1110 over the taggant 1105, the label 1115 can be irradiated with electromagnetic energy in a specific pattern, such as an alphanumeric code, a computer readable code, an image, etc., in order to at least partially cure the irradiated portion of the adhesive 1125. The at least partially cured portion of the adhesive 1125 will trap or adhere more tightly to the taggant 1105 distributed on the object 1110 such that when the label 1115 is removed from the object 1110, a pattern of the taggant 1105 adheres to the at least partially cured adhesive 1125 and is removed along with the label 1115.

In some embodiments, the pattern of the taggant 1105 in the adhesive 1125 can correspond to a predetermined or recognizable pattern used for authentication of the label 1115 as described elsewhere herein. In some embodiments, the taggant 1105 may form a first pattern on the object, where the first pattern is a specific, recognizable pattern stored in a memory. When the label 1115 is removed from the object 1110 taking only a portion of the taggant 1105, the pattern of the taggant 1105 that is removed with the label can form a second pattern, which is specific and recognizable to a detector for authentication.

In the above embodiments, counterfeit labels 1115 can be detected. For example, a counterfeiter may buy or obtain a label 1115 on the object 1110, such as on the backing of an adhesive stamp. The counterfeiter may interrogate the label 1115 on the object 1110 to determine what the pattern of the taggant 1105 is in order to reproduce it. However, if these counterfeit labels 1115 are produced with the pattern of the taggant 1105 as revealed on the object 1110, when the label 1115 is removed from the object 1110, the pattern of the taggant 1105 on the label 1115 will change, as some of the taggant 1105 adheres to the label 1115 and some does not. If a label interrogation device, as described above, interrogates a label on an object and detects the pattern of the taggant 1105 associated with the label 1115 being on the object 1110, then the counterfeit label and method of counterfeiting can be detected.

In some embodiments, the taggant 1105 and the adhesive 1125 can be used to create a short-term authentication system. A short-term authentication system can be a system where the taggant 1105 forms a recognizable emission pattern for a limited time, effectively providing an expiration date for the label 1115. To create a short-term verification, a taggant and an adhesive can be chosen having the correct properties. The taggant 1105 can have a buoyancy in the adhesive 1125 such that the taggant 1105 will settle or sink through the adhesive toward the object 1110 over time. To generate the short-term verification system, the taggant 1105 can be applied to the substrate 1120. The adhesive 1125 can be applied to the substrate 1120. When the label 1115 is applied to the object 1110 and oriented with the label 1115 facing up, the viscosity of the adhesive and the buoyancy of the taggant 1105 will cause the taggant 1105 to slowly drift through the adhesive. The taggant 1105 can emit an emission pattern only a short distance, and, as the taggant 1105 drifts, the distance drifted through the adhesive 1125 can be greater than the detectable emission pattern. Thus, when the label 1115 is manufactured, the taggant 1105 can be arranged in a recognizable pattern, but as time passes, the taggant 1105 migrates through the adhesive such that the taggants 1105 are farther away from the substrate 1120, and upon interrogation, the emission pattern from the taggants 1105 is not detectable through the substrate 1120. In some embodiments, the emission pattern from the taggant 1105 is not recognized by the detector, or in other words, cannot be authenticated, because the emission pattern does not meet a minimum threshold for brightness, due to the migration of the taggant 1105 through the adhesive 1125. In some embodiments, the emission pattern is not recognized because the pattern has been distorted due to the migration of the taggant 1105 through the adhesive 1125.

In some embodiments, more than one type of taggant 1105 can be used, where the different types of taggants have different buoyancies in the adhesive 1125. In some embodiments, different adhesives 1125 can be applied to the substrate having different viscosities, such that the taggant 1105 will migrate differently in the different types of adhesive 1125. Over time the emission pattern detected by the detector will change as the taggant 1105 migrates through the adhesive 125. Thus, as time passes, the migration of the taggant 1105 will cause the label 1115 to lose its ability to be verified by the detector and the interrogation signal. The expiration time for the label 1115 can be established by selecting the adhesive 1125 and/or the taggant 1105 having the viscosity and buoyancy.

FIG. 12 depicts one embodiment of an item validation system having a matrix 1200 of authentication cells 1250. In some embodiments, cell walls 1255 can be a structural part of the label 1115 or the object 1110, while in other embodiments, cell walls 1255 are non-tangible delineations. For example, the label 1115 may have cell walls 1255 situated in the adhesive 1125 and/or extending from the substrate 1120 to form separate cells 1250 in the adhesive 1125. The cell walls 1255 can prevent the taggant 1105 in the adhesive 1125 from moving or drifting into other cells 1250. In some embodiments, each cell 1250 may contain one or more discrete adhesive areas 210 and have cell walls 1255. In this example, one or more of the adhesive areas 210 may contain one or more taggants 1105. A matrix 1200 of cells 1250 may cover all or a portion of an area of a label 1115. In an example, a matrix 1200 may be a 100×100 comprising 10,000 cells 1250.

Cells 1250 may be indicative of portions of an object 1110 where taggants 1105 are printed. For example, one or more taggants 1105 may be printed on an object 1110 for each area of the object 1110 defined by one cell 1250 area. As shown in FIG. 11, a label 1115 may be in contact with the object 1110. As described above, the pattern or number or type of the of taggants 1105 in the matrix 1200 are peeled off with the label 1115 can be controlled. In this way, a specified pattern of taggants 1105 may be situated in the label 1115.

The matrix 1200 of cells 1250 can have the taggant 1105 selectively applied thereto. The pattern of the taggant 1105 applied to the individual cells 1250 can correspond to a specific or predetermined recognizable pattern. In addition, the pattern of cells 1250 to which the specific pattern of taggant 1105 is applied can correspond to a specific or predetermined recognizable pattern. This results in two separate recognizable patterns of the taggant 1105. For example, the taggant 1105 may be applied to one or more of the cells 1250, where the taggant 1105 is applied in a predetermined pattern, such as an alphanumeric code or image. The predetermined pattern of the taggant 1105 can then be applied to selected cells 1250 of the matrix 1200. As depicted in FIG. 12, the predetermined pattern of the taggant 1105 is applied to cells (1,1), (1,2), (2,3), etc. The label 1115 is applied to the matrix 1200, and the taggant 1105 adheres to the label 1115. Upon interrogation by an excitation signal, two recognizable patterns should be identified: first, the interrogation can recognize the specific pattern of the taggant 1105 applied in each of the cells 1250, and can also recognize the overall pattern of cells 1250 in the matrix 1200 which have the taggant 1105 therein. This can provide two layers of verification.

In some embodiments, the cells 1250 may have different patterns of the taggant 1105 therein, which pattern is also stored and recognizable by a detector as described elsewhere herein.

In some embodiments, the taggant 1105 is conditionally "active" or "inactive." An inactive taggant is one that, when interrogated or exposed to an excitation signal, does not provide a suitable response. An active taggant does provide a response when interrogated or exposed to an excitation signal In some instances, the state of an inactive or active taggant 1105 may be changed by curing the taggant 1105. Curing may comprise any suitable method for altering the properties of a taggant 1105, for example, irradiating the taggant 1105 with light at a certain wavelength, heating the taggant 1105, and the like. In response to such curing, an inactive taggant 1105 may become active, that is, it may provide a suitable response to interrogation.

In some embodiments, taggants in the adhesive layer 1125 and/or printed on an object 1110 may be inactive. A user and/or machine may selectively activate and/or cure one or more of the taggants 1105. For example, one or more inactive taggants 1105 may be situated in adhesive areas 210 of a label 1115, with one adhesive area 210 for each cell 1250 of a matrix 1200. The taggants 1105 may selectively be activated using a curing process to create a specific pattern of activated taggants 1105. In this way, when the label 1115 is interrogated, the specified pattern of taggants 1105 will be shown.

In another embodiment, the cells 1250 of FIG. 12 may correspond to areas of a label 1115 that may or may not be imprinted with ink. For example, a substrate 1120 may be imprinted with ink at various portions, each portion corresponding to a cell 1250 of a matrix 1200. In this way, the ink printed on the substrate 1120 may form a pattern. In an embodiment, the ink may be configured to reflect radiated light. In one example, the ink may reflect light of only a certain wavelength, and not reflect light of other wavelengths. When the label 1115 is irradiated with light of a specified wavelength, the pattern of ink may reflect light (e.g., an excitation signal) onto other portions of the label 1115 (e.g., an adhesive layer 1125). The reflected light may then excite and/or reflect off of taggants 1105 in the adhesive layer 1125 in a pattern corresponding to the ink pattern. The excitation or emission pattern may then be detected and analyzed for accuracy.

In some embodiments, the adhesive 1125 may include a multiplier particle (not shown), such as a reflective metal strip, or other reflective particle. As the excitation signal contacts the multiplier particle, the multiplier particle can scatter, concentrate, or focus the excitation signal toward a specific area of the adhesive in order to increase or strengthen a signal emitted from the taggant 1105 in the specific area. The multiplier particle can be used to make portions of the taggant 1105 and thus the resulting emission pattern brighter than other portions of the pattern of the taggant 1105. The difference between the brightness of the various portions of the taggant 1105 or the emission pattern can be specific and recognizable to the detector. To authenticate a label having an adhesive with multiplier particles, the detector must detect the specific pattern of brightness due to the multiplier particles.

In some embodiments the multiplier particles can be configured or arranged to reflect or diffuse light, such as deeper into the adhesive 1125 or toward the object 1110, which has the effect of dimming or weakening the emission from the taggant 1105 upon interrogation of the label 1115. The multiplier particles can be arranged within the adhesive 1125 in order to create a specific pattern of dim areas in the emission pattern of the taggant 1105 in response to the interrogation signal. In some embodiments, the multiplier particles can be used both to brighten certain parts of the emission pattern and to dim or darken other portions of the emission pattern. In some embodiments the multiplier particles are configured to absorb the interrogation signal to create a recognizable, specific pattern of darker or dimmer areas in the emission pattern.

Figure 13:
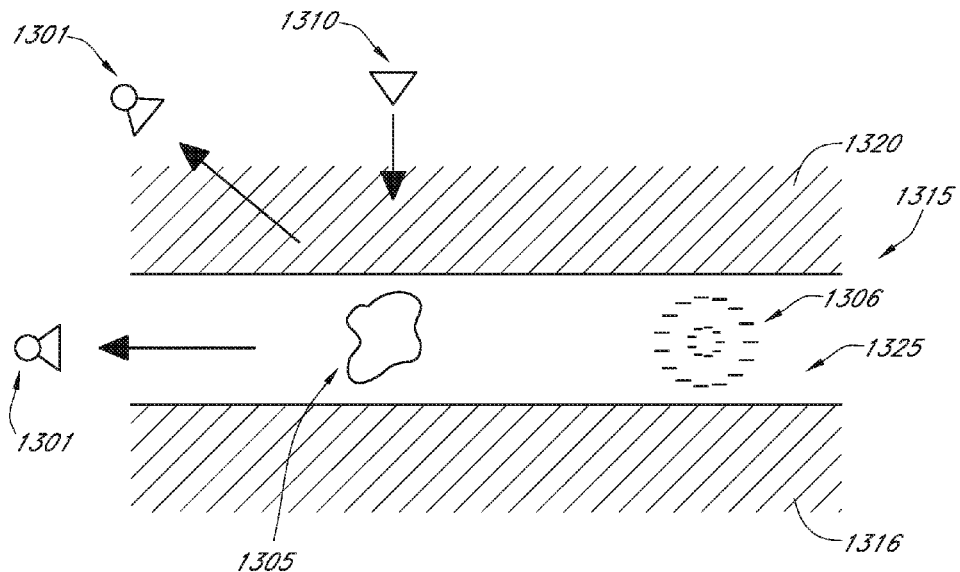
FIG. 13 is a cross-sectional view of another embodiment of a validation system having multiple receivers for detecting responses from a taggant.

FIG. 13 depicts one embodiment of a validation system having multiple receivers 1301 for detecting responses from a taggant 1305. In this embodiment, a detector 1310 may interrogate the taggant 1305. The taggant 1305 may be distributed in various shapes and patterns, and the particles of the taggant 1305 may have various shapes and sizes. For example, the particles of the taggant 1305 may be distributed in an adhesive 1325 both vertically and horizontally such that the particles of the taggant 1305 are arranged to generate different emission patterns a viewpoint of the receiver 1301 or the position of the detector which emits the interrogation signal. Also, during interrogation, he taggant 1305 may reflect light in various directions. As a result, one or more of the multiple receivers 1301 may capture emitted and/or reflected light from the taggant 1305. Also, each receiver 1301 may capture a different pattern from the taggant 1305 based on the viewpoint of the receiver 1301. If one particular image of a taggant 1305 is desired, using multiple receivers 1301 may improve chances of detecting the desired image. Moreover, some taggants 1305 may be interrogated from any angle.

In some embodiments, a taggant pattern 1306 may be composed of multiple layers of particles of the taggant 1305.

For example, an adhesive layer 1125 may have multiple, distinct layers which can be individually applied to a substrate 1320 to form a label 1315, with a portion of the taggant 1305 required to form the taggant pattern 1306 disposed within each of the multiple layers. The particles of the taggant 1305 are thus distributed throughout the adhesive to form the taggant pattern 1306. The taggant pattern 1306 can form a recognizable pattern when interrogated through the label as described elsewhere herein. The taggant pattern 1306 can also form a recognizable pattern when interrogated from the side, that is, when interrogated in a direction parallel to the plane of the substrate 1320 and an object 1316 on which the label 1315 is placed. In some embodiments, the detector and interrogation signal are directed at the side of the adhesive layer, and the excitation or interrogation signal causes the taggant pattern 1306 to emit a recognizable emission pattern. In some embodiments, the authentication can require recognition of the taggant pattern 1306 through the label as described above, along with recognition of the taggant pattern 1306 viewed from the side of the adhesive layer.

In some embodiments, the taggant pattern 1306 of particles of the one or more types of taggant 1305 can be disposed at certain depths in the adhesive in order to generate a holographic image, which is recognizable to a detector upon interrogation with an interrogation signal.

In some embodiments, the taggant pattern 1306, or any other distribution of taggants described herein, may also be composed of multiple particles or fibers having variable densities. The pattern or arrangement of the particles or fibers of the taggant 1305 can be controlled by a heat-pressing process. For example, by use of a heat press, the particles or fibers of the taggant 1305 in one area may be pressed/concatenated together. The heat press may be applied in a pattern to the label 1315 or with varying degrees of heat and/or pressure to create a distribution of the taggant 1305 in the adhesive which forms a recognizable pattern. In some embodiments, the heat pressing can create the taggant pattern 1306 by concentrating/concatenating particles of the taggant 1305 throughout the depth of the adhesive 1325, or, in other words, along an axis perpendicular to the label 1315 or the object 1316 on which the label 1315 is attached. In some embodiments, the heat pressing can be performed during application of the adhesive 1325 to a substrate. In some embodiment the heat pressing can be performed after the adhesive layer may have varying dimensions and may appear three-dimensional.

Figure 14:
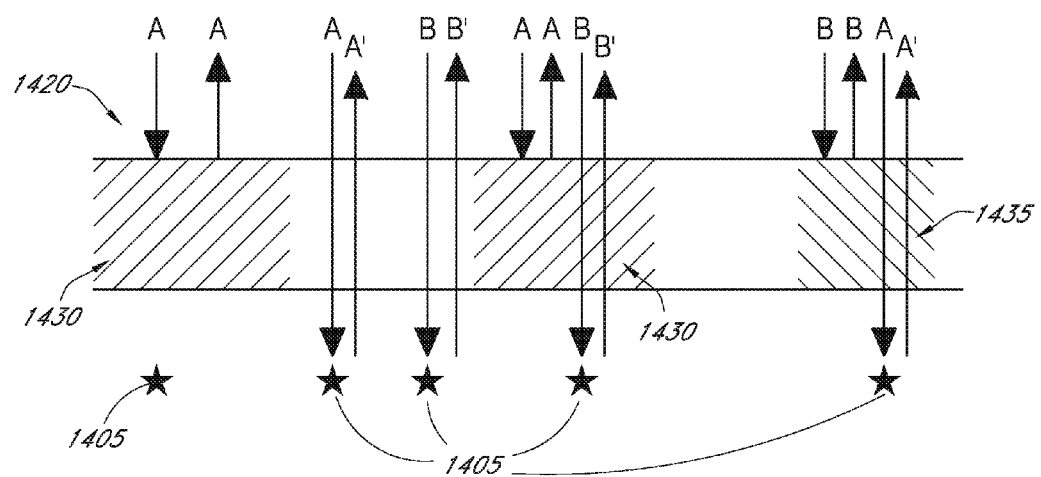
FIG. 14 is a cross-sectional view of a substrate having a first ink and a second ink which permit light at certain wavelengths to pass through while being opaque to light at other wavelengths.

In some embodiments, a validation system may use various inks. FIG. 14 depicts a substrate, printed material, or other area 1420 having a first ink 1430 and a second ink 1435 both of which can permit light at certain wavelengths to pass through while resisting light at other wavelengths. For example, light A has a first wavelength, is not be able to pass through the first ink 1430 but is able to pass through a second ink 1435. Light B has a second wavelength, different from light A, which is not transmitted by the second ink 1435, but is transmitted through the first ink 1430. That is, if light at wavelength, A, is directed on the substrate 1420, the light A, is not transmitted by the first ink 1430, but is transmitted through the second ink 1435. Thus, a taggant 1405 under the first ink 1430 will not be excited by the light A, The taggant 1405 under the second ink 1435 will be excited by the light A. The taggant 1405 excited by the light A can emit light at a wavelength A', which can be detected by the detector.

If light at wavelength B, is directed on the substrate 1420, the light B, is not transmitted by the second ink 1435, but is transmitted through the first ink 1430. Thus, a taggant 1405 under the second ink 1435 will not be excited by the light B, The taggant 1405 under the first ink 1430 will be excited by the light B. The taggant 1405 excited by the light B can emit light at a wavelength B', which can be detected by the detector. In some embodiments, the first ink 1430 and the second ink 1435 can pass both light A and B, but may be selectively opaque to the emitted light A' and B'. In this way, the first ink and second ink 1430 and 1435 can create a pattern in the emitted light from the taggant 1405. in some embodiments, an interrogation signal can contain both light A and light B. the pattern of the first ink 1430 and the pattern of the second ink 1435 will variously transmit light A and light B, resulting in a specific emission pattern of light A' and B'. The first and second inks 1430 and 1435 can be applied to the substrate 1420 in order to create a desired, specific, recognizable emission pattern from the taggant 1405 upon interrogation with both light A and light B. In some embodiments, the first ink 1430 and the second ink 1435 can be a substance or material coated or applied to the substrate 1405 which has the same effect of passing certain wavelengths and reflecting certain other wavelengths as described above.

In another embodiment, one or more layers may have varying fiber densities. For example, an ink 1430 portion may have multiple fibers having variable densities. Fibers having higher densities may be more restrictive to an interrogation signal and/or be restrictive to different kinds of light than fibers having lower densities. In another example individual fibers of an ink 1430 portion may be angled, which may further affect the behavior of an interrogation signal. The fiber density may be affected by an embossing process used in printing the ink 1430.

Some embodiments may use foils or other materials to multiply and/or otherwise affect radiated light. For example, an object 1110 may have foil printed on its surface. Irradiated light that passes through the adhesive 1125 layer may reach the foil. The foil may receive the particles of light and may reflect a modified beam of light in response to the incident light.

As described elsewhere herein, some labels 1115 may be time-sensitive, or have short-term validity. For example, taggants 1105 in an adhesive layer 1125 may migrate (i.e., change positions) over time, causing a pattern to become distorted. This migration may be caused by gravity, heat, etc. In another example, taggants 1105 may precipitate out of the adhesive layer 1125 over time. This may be caused by, for example, a dye in an alcohol solution that precipitates when the alcohol evaporates.

Taggants 1105 may be composed of a variety of materials, including solids, liquids, gases, etc. In one example, a taggant 1105 may have a solid outer layer and be filled with a liquid and/or gas. In another example, a taggant 1105 may be entirely composed of a liquid.

The technology is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, processor-based systems, programmable consumer electronics, network PCs, minicomputers, mainframe computers, distributed computing environments that include any of the above systems or devices, and the like.

As used herein, instructions refer to computer-implemented steps for processing information in the system.

Instructions can be implemented in software, firmware or hardware and include any type of programmed step undertaken by components of the system.

A processor may be any conventional general purpose single- or multi-chip processor such as a Pentium® processor, a Pentium® Pro processor, a 8051 processor, a MIPS® processor, a Power PC® processor, or an Alpha® processor. In addition, the processor may be any conventional special purpose processor such as a digital signal processor or a graphics processor. The processor typically has conventional address lines, conventional data lines, and one or more conventional control lines.

The system is comprised of various modules as discussed in detail. As can be appreciated by one of ordinary skill in the art, each of the modules comprises various sub-routines, procedures, definitional statements and macros. Each of the modules are typically separately compiled and linked into a single executable program. Therefore, the description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system may be used in connection with various operating systems such as Linux®, UNIX® or Microsoft Windows®.

The system may be written in any conventional programming language such as C, C++, BASIC, Pascal, or Java, and ran under a conventional operating system. C, C++, BASIC, Pascal, Java, and FORTRAN are industry standard programming languages for which many commercial compilers can be used to create executable code. The system may also be written using interpreted languages such as Perl, Python or Ruby.

Those of skill will further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In one or more example embodiments, the functions and methods described may be implemented in hardware, software, or firmware executed on a processor, or any combination thereof. If implemented in software, the functions may be stored on or transmitted over as one or more instructions or code on a computer-readable medium. Computer-readable media include both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. An item comprising:
   a backing;
   a taggant disposed on the backing, the taggant arranged in a first pattern;
   an adhesive layer in contact with at least a portion of the backing;
   a label disposed on the adhesive layer;
   wherein the adhesive layer is configured to adhere to the label and to a first portion of the taggant disposed on the backing in order to form a predetermined second pattern on the adhesive layer when the label is detached from the backing, and wherein the adhesive layer is configured to detachably adhere to a second portion of the taggant and to the backing such that the adhesive layer and the label remain substantially intact when the label is removed from the backing and such that the label and adhesive can be subsequently adhered to an object; and
   wherein the taggant is configured to emit a luminescence in response to an excitation signal, the emitted luminescence of the first pattern on the adhesive layer being detectable and recognizable by a detector when the label is on the backing, and the emitted luminescence of the second pattern on the adhesive layer being detectable and recognizable by a detector when the label is detached from the backing.

2. The item of claim 1, wherein the emitted luminescence from the second pattern is a computer readable code.

3. The item of claim 1, wherein the taggant comprises a first set of taggants and a second set of taggants, and wherein only the first set of taggants is configured to combine with the adhesive layer such that the first set of taggants is removed with the label when the adhesive layer detaches from the backing.

4. The item of claim 1, wherein the adhesive comprises a photocurable adhesive, and wherein the taggant adheres to the adhesive layer upon curing of the adhesive.

5. The item of claim 1, wherein the adhesive layer is curable upon illuminating the adhesive with light, and wherein the pattern of light used to cure the photocurable adhesive corresponds to the second pattern.

6. The item of claim 1, wherein the taggant comprises a first taggant and a second taggant, the first and second taggants having different solubility in the adhesive.

7. The item of claim 6, wherein the first taggant is soluble in the adhesive and adheres to the adhesive.

8. The item of claim 7, wherein the first taggant is applied to the backing in a form corresponding to the second pattern.

9. A method of creating an item comprising:
   disposing a taggant on a backing, the taggant forming a first pattern;
   disposing an adhesive layer onto at least a portion of the backing;
   disposing a label on the adhesive layer; and
   adhering the adhesive layer to a portion of the taggant disposed on the backing in order to form a predetermined second pattern on the adhesive layer when the adhesive layer is detached from the backing, wherein the adhesive layer is configured to detachably adhere to the portion of the taggant and to the backing such that the adhesive layer and the label remain substantially intact when the label is removed from the backing and such that the label and the adhesive layer can be subsequently adhered to an object, and wherein the taggant is configured to emit a luminescence in response to an excitation signal.

10. The method of claim 9, wherein the adhesive layer comprises a photo-curable adhesive, and wherein forming a second pattern comprises irradiating the adhesive layer to an extent sufficient to adhere the taggant to the adhesive in the second pattern.

11. The method of claim 9, wherein the taggant comprises a first taggant and a second taggant, the first and second taggants having different solubility in the adhesive.

12. The method of claim 11, wherein the first taggant is applied to the backing in a form corresponding to the predetermined second pattern and wherein forming the second pattern comprises dissolving the first taggant in the adhesive layer according to the solubility of the first taggant.

13. The method of claim 9, wherein the emitted luminescence of the predetermined second pattern forms a computer readable code.

14. A method of making a label comprising:
preparing a backing;
disposing a taggant on the backing, wherein the taggant is disposed in a first pattern, the taggant being configured to emit a luminescence in response to an excitation signal;
applying an adhesive to the backing to form an adhesive layer;
applying a substrate to the adhesive layer, the adhesive layer and substrate together forming a label; and
selectively adhering a portion of the taggant to the adhesive layer, the portion of the taggant being adhered to form a predetermined second pattern when the label is detached from the backing, and wherein the adhesive layer is selectively adhered such that the substrate and the adhesive layer remain intact when the label is detached from the backing and such that the label and the adhesive can be subsequently adhered to an object.

15. The method of claim 14, wherein the adhesive is a photocurable polymer.

16. The method of claim 15, wherein the luminescence emitted by the taggant in the first pattern and in the second pattern are recognizable patterns for authentication of the label.

17. The method of claim 14, wherein selectively adhering a portion of the taggant to the adhesive comprises irradiating the adhesive in a pattern corresponding to the second pattern.

18. The method of claim 14, wherein the taggant comprises a first taggant and a second taggant, the second taggant being applied according to the predetermined second pattern, and wherein the first and second taggant have different diffusivities in the adhesive.

19. The method of claim 18, wherein selectively adhering a portion of the taggant to the adhesive comprises diffusing relatively more of the second taggant into the adhesive and relatively less of the first taggant into the adhesive.

* * * * *